US012521152B2

(12) United States Patent
Armstrong et al.

(10) Patent No.: US 12,521,152 B2
(45) **Date of Patent: *Jan. 13, 2026**

(54) SPINAL IMPLANT SYSTEM AND METHOD

(71) Applicant: Warsaw Orthopedic, Inc., Warsaw, IN (US)

(72) Inventors: Rex W. Armstrong, Memphis, TN (US); William Alan Rezach, Memphis, TN (US)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 1213 days.

This patent is subject to a terminal disclaimer.

(21) Appl. No.: 17/301,550

(22) Filed: Apr. 6, 2021

(65) Prior Publication Data

US 2021/0220018 A1 Jul. 22, 2021

Related U.S. Application Data

(63) Continuation of application No. 15/337,229, filed on Oct. 28, 2016, now Pat. No. 10,966,760.

(51) Int. Cl.
*A61B 17/70* (2006.01)

(52) U.S. Cl.
CPC ........ *A61B 17/705* (2013.01); *A61B 17/7037* (2013.01)

(58) Field of Classification Search
CPC ............ A61B 17/7007; A61B 17/7008; A61B 17/7011; A61B 17/7038; A61B 17/7041; A61B 17/7043; A61B 17/7049; A61B 17/705; A61B 17/7052
See application file for complete search history.

(56) References Cited

U.S. PATENT DOCUMENTS

| | | | |
|---|---|---|---|
| 5,207,678 | A | 5/1993 | Harms et al. |
| 5,575,792 | A | 11/1996 | Errico et al. |
| 5,609,593 | A | 3/1997 | Errico et al. |
| 5,609,654 | A | 3/1997 | Le et al. |
| 5,630,817 | A | 5/1997 | Rokegem et al. |
| 5,643,263 | A | 7/1997 | Simonson |
| 5,797,911 | A | 8/1998 | Sherman et al. |
| 5,885,285 | A | 3/1999 | Simonson |

(Continued)

FOREIGN PATENT DOCUMENTS

| | | |
|---|---|---|
| CN | 101594832 | 12/2009 |
| CN | 102596067 | 7/2012 |

(Continued)

OTHER PUBLICATIONS

Translation of DE 202011107821 U1 (Year: 2012).*

(Continued)

*Primary Examiner* — Lynnsy M Summitt
(74) *Attorney, Agent, or Firm* — Sheridan Ross P.C.

(57) ABSTRACT

A spinal construct includes a coupling member including a first mating surface engageable with an existing fastener implant. The existing fastener implant being connected with an existing spinal rod implant. A connector is engageable with the existing fastener implant and has a rod extending therefrom. A locking member is engageable with a second mating surface of the coupling member. Systems, surgical instruments, implants and methods are disclosed.

17 Claims, 13 Drawing Sheets

(56) References Cited

U.S. PATENT DOCUMENTS 5,885,286 A 3/1999 Sherman et al.
5,947,967 A 9/1999 Barker
6,022,350 A 2/2000 Ganem
6,063,090 A 5/2000 Schlapfer
6,074,391 A 6/2000 Metz-Stavenhagen et al.
6,226,548 B1 5/2001 Foley et al.
6,280,422 B1 * 8/2001 Sanchez-Browning .................... A61M 5/16877 215/11.4
6,280,442 B1 8/2001 Barker et al.
6,520,962 B1 2/2003 Taylor et al.
6,562,038 B1 5/2003 Morrison
6,565,566 B1 5/2003 Wagner et al.
6,572,618 B1 6/2003 Morrison
6,579,292 B2 6/2003 Taylor
6,648,887 B2 11/2003 Ashman
6,685,705 B1 2/2004 Taylor
6,755,830 B2 6/2004 Minfelde et al.
6,872,209 B2 3/2005 Morrison
7,066,939 B2 6/2006 Taylor
7,867,255 B2 * 1/2011 Miller .................. A61B 17/705 606/279
7,976,567 B2 7/2011 Null et al.
8,021,397 B2 9/2011 Farris et al.
8,034,089 B2 10/2011 Matthis et al.
8,097,025 B2 1/2012 Hawkes et al.
8,167,025 B2 5/2012 Rombs et al.
8,197,518 B2 6/2012 Hammill, Sr.
8,197,910 B2 6/2012 Chen et al.
8,277,489 B2 10/2012 Saidha et al.
8,298,265 B2 10/2012 Purcell et al.
8,298,275 B2 10/2012 Rezach
8,419,773 B2 4/2013 Biedermann et al.
8,430,913 B2 4/2013 James et al.
8,523,911 B2 * 9/2013 Jani .................... A61B 17/7032 606/264
8,556,938 B2 * 10/2013 Jackson ............. A61B 17/7008 606/264
8,585,741 B2 11/2013 Gabelberger et al.
8,672,978 B2 3/2014 Dant et al.
8,795,337 B2 8/2014 Wilcox et al.
8,992,575 B1 3/2015 Di Lauro et al.
8,998,959 B2 4/2015 Jackson et al.
9,155,580 B2 10/2015 Cormier et al.
9,247,964 B1 2/2016 Shoshtaev
9,314,274 B2 4/2016 Amstutz et al.
9,387,013 B1 7/2016 Shoshtaev et al.
9,402,663 B2 8/2016 Peterson et al.
9,615,858 B2 4/2017 Doubler et al.
9,629,663 B2 4/2017 Ludwig et al.
9,788,865 B2 10/2017 Matthis et al.
9,820,782 B2 11/2017 Daniels
9,924,975 B2 3/2018 Jackson et al.
10,188,432 B2 1/2019 Jackson et al.
10,238,432 B2 3/2019 Carruth et al.
10,413,331 B2 9/2019 Gregory
10,543,021 B2 1/2020 Jackson et al.
10,736,665 B2 8/2020 Bobbitt et al.
10,835,291 B2 11/2020 May
10,966,760 B2 4/2021 Armstrong et al.
11,109,895 B2 9/2021 May et al.
11,219,471 B2 1/2022 Jackson et al.
11,291,477 B1 4/2022 Rezach et al.
11,890,033 B1 2/2024 McBride et al.
2002/0029040 A1 3/2002 Morrison et al.
2002/0143341 A1 10/2002 Biedermann et al.
2004/0162558 A1 8/2004 Hegde et al.
2005/0049588 A1 3/2005 Jackson
2005/0228326 A1 * 10/2005 Kalfas ................ A61B 17/7007 602/19
2005/0240180 A1 10/2005 Vienney et al.
2005/0273101 A1 12/2005 Schumacher
2006/0058794 A1 3/2006 Jackson
2006/0083603 A1 4/2006 Jackson
2006/0241600 A1 10/2006 Ensign et al.
2007/0055244 A1 3/2007 Jackson
2007/0135817 A1 6/2007 Ensign et al.
2007/0191840 A1 8/2007 Pond, Jr. et al.
2007/0270805 A1 * 11/2007 Miller .................. A61B 17/705 606/255
2007/0270839 A1 11/2007 Jeon et al.
2007/0288004 A1 12/2007 Alvarez
2008/0015584 A1 1/2008 Richelsoph
2008/0177323 A1 * 7/2008 Null ..................... A61B 17/705 606/267
2008/0183215 A1 7/2008 Altarac et al.
2008/0262553 A1 10/2008 Hawkins et al.
2008/0294194 A1 * 11/2008 Capote ............... A61B 17/7037 606/100
2010/0087864 A1 4/2010 Klein et al.
2010/0087867 A1 * 4/2010 Klein ................. A61B 17/7049 606/279
2010/0094345 A1 4/2010 Saidha et al.
2010/0160981 A1 6/2010 Butler et al.
2010/0318131 A1 12/2010 James et al.
2010/0324599 A1 * 12/2010 Montello ........... A61B 17/7007 606/279
2011/0040338 A1 2/2011 Jackson
2011/0093021 A1 4/2011 Fanger et al.
2011/0098755 A1 4/2011 Jackson et al.
2011/0257690 A1 10/2011 Rezach
2011/0270325 A1 11/2011 Keyer et al.
2012/0046701 A1 2/2012 Gennari et al.
2012/0101533 A1 4/2012 Purcell et al.
2012/0109208 A1 5/2012 Justis et al.
2012/0109218 A1 5/2012 Farris
2012/0130436 A1 5/2012 Haskins et al.
2014/0214084 A1 7/2014 Jackson et al.
2015/0351809 A1 12/2015 Jackson et al.
2016/0015429 A1 1/2016 Butler
2016/0166289 A1 6/2016 Alsup et al.
2016/0206357 A1 7/2016 Whipple
2016/0262798 A1 9/2016 Rezach et al.
2016/0367292 A1 12/2016 Nichols et al.
2017/0245898 A1 8/2017 May et al.
2017/0281241 A1 10/2017 Jackson et al.
2017/0348026 A1 12/2017 Stein et al.
2018/0206890 A1 7/2018 Rezach
2018/0228516 A1 8/2018 Armstrong et al.
2018/0228518 A1 8/2018 Carruth et al.
2018/0243009 A1 8/2018 Bobbitt et al.
2019/0029729 A1 1/2019 Mire et al.
2020/0146724 A1 5/2020 Italiaie
2021/0153904 A1 5/2021 Armstrong et al.
2021/0169531 A1 6/2021 Leff et al.
2021/0401468 A1 12/2021 May et al.
2024/0138881 A1 5/2024 Armstrong et al.
2024/0188992 A1 6/2024 Dewey et al.

FOREIGN PATENT DOCUMENTS

CN 202932996 3/2013
CN 103025255 4/2013
CN 103153219 6/2013
DE 202011107821 2/2012
DE 202011107821 U1 * 4/2012 ......... A61B 17/7007
DE 102011111403 10/2012
EP 3579770 12/2019
FR 2859620 3/2005
WO WO 2014/138614 9/2014

OTHER PUBLICATIONS

Coric et al., "Percutaneous, Navigated Minimally Invasive Posterior Cervical Pedicle Screw Fixation," International Journal of Spine Surgery, vol. 14, Suppl. 3, Dec. 9, 2020, pp. S14-S21.
Coric et al., "Percutaneous Posterior Cervical Pedicle Instrumentation (C1 to C7) With Navigation Guidance: Early Series of 27 Cases," Global Spine Journal, vol. 12, No. 2S, pp. 27S-33S.

(56) References Cited

OTHER PUBLICATIONS

International Search Report and Written Opinion for International (PCT) Patent Application No. PCT/IB2023/062256, dated Mar. 20, 2024, 16 pages.
International Search Report and Written Opinion for International (PCT) Patent Application No. PCT/IB2023/060616, dated Jan. 29, 2024, 13 pages.
Official Action for China Patent Application No. 201810132125.8, dated Jan. 10, 2022, 22 pages.
Article 94(3) Communication for Europe Patent Application No. 18152721.9, dated Jun. 18, 2021, 7 pages.
Article 94(3) Communication for Europe Patent Application No. 18152721.9, dated Mar. 15, 2023, 4 pages.
Official Action for U.S. Appl. No. 17/976,163, dated Jun. 26, 2023, 12 pages.
Notice of Allowance for U.S. Appl. No. 17/976,163, dated Oct. 2, 2023, 5 pages.
Official Action for U.S. Appl. No. 15/337,229, dated May 11, 2017, 12 pages.
Official Action for U.S. Appl. No. 15/337,229, dated Dec. 14, 2017, 12 pages.
Official Action for U.S. Appl. No. 15/337,229, dated Apr. 3, 2018, 13 pages.
Official Action for U.S. Appl. No. 15/337,229, dated Oct. 19, 2018, 18 pages.
Official Action for U.S. Appl. No. 15/337,229, dated Apr. 3, 2019, 19 pages.
Official Action for U.S. Appl. No. 15/337,229, dated Oct. 11, 2019, 7 pages.
Official Action for U.S. Appl. No. 15/337,229, dated Feb. 7, 2020, 21 pages.
Notice of Allowance for U.S. Appl. No. 15/337,229, dated Dec. 11, 2020, 5 pages.
Official Action for U.S. Appl. No. 15/432,704, dated Aug. 1, 2018, 6 pages. Restriction Requirement.
Official Action for U.S. Appl. No. 15/432,704, dated Oct. 15, 2024, 10 pages.
Official Action for U.S. Appl. No. 15/432,704, dated Apr. 22, 2019, 23 pages.
Official Action for U.S. Appl. No. 15/432,704, dated Oct. 30, 2019, 25 pages.
Official Action for U.S. Appl. No. 15/432,704, dated Feb. 4, 2020, 26 pages.
Official Action for U.S. Appl. No. 15/432,704, dated May 13, 2020, 21 pages.
Official Action for U.S. Appl. No. 15/432,704, dated Sep. 18, 2020, 21 pages.
Official Action for U.S. Appl. No. 15/432,704, dated Feb. 24, 2021, 30 pages.
Official Action for U.S. Appl. No. 15/432,704, dated Jul. 28, 2021, 27 pages.
Official Action for U.S. Appl. No. 15/432,704, dated Oct. 28, 2021, 32 pages.
Official Action for U.S. Appl. No. 15/432,704, dated Dec. 17, 2021, 29 pages.
Official Action for U.S. Appl. No. 17/163,896, dated Nov. 23, 2022, 28 pages.
Official Action for U.S. Appl. No. 17/163,896, dated May 12, 2023, 29 pages.
Official Action for U.S. Appl. No. 17/163,896, dated Aug. 24, 2023, 32 pages.
Official Action for U.S. Appl. No. 17/163,896, dated Dec. 27, 2023, 31 pages.
Official Action for U.S. Appl. No. 17/163,896, dated May 28, 2024, 42 pages.
Official Action for U.S. Appl. No. 17/163,896, dated Oct. 18, 2024, 45 pages.
Official Action for U.S. Appl. No. 15/334,873, dated Apr. 19, 2018, 12 pages.
Official Action for U.S. Appl. No. 15/334,873, dated Nov. 20, 2018, 15 pages.
Official Action for U.S. Appl. No. 15/334,873, dated May 3, 2019, 6 pages.
Official Action for U.S. Appl. No. 15/334,873, dated Oct. 11, 2019, 9 pages.
Official Action for U.S. Appl. No. 15/334,873, dated Sep. 15, 2020, 11 pages.
Official Action for U.S. Appl. No. 15/334,873, dated Jan. 6, 2021, 15 pages.
Advisory Action for U.S. Appl. No. 15/334,873, dated Mar. 11, 2021, 5 pages.
Notice of Allowance for U.S. Appl. No. 15/334,873, dated May 11, 2021, 9 pages.
Official Action for U.S. Appl. No. 17/468,597, dated Oct. 23, 2024, 15 pages.
Notice of Allowance for U.S. Appl. No. 17/468,597, dated Mar. 10, 2025, 8 pages.

* cited by examiner

SPINAL IMPLANT SYSTEM AND METHOD

CROSS REFERENCE TO RELATED APPLICATIONS

This application is a continuation of U.S. patent application Ser. No. 15/337,229, filed Oct. 28, 2018, which is expressly incorporated by reference herein, in its entirety.

TECHNICAL FIELD

The present disclosure generally relates to medical devices for the treatment of musculoskeletal disorders, and more particularly to a spinal implant system and a method for treating a spine.

BACKGROUND

Spinal pathologies and disorders such as scoliosis and other curvature abnormalities, kyphosis, degenerative disc disease, disc herniation, osteoporosis, spondylolisthesis, stenosis, tumor and fracture may result from factors including trauma, disease and degenerative conditions caused by injury and aging. Spinal disorders typically result in symptoms including deformity, pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes correction, fusion, fixation, discectomy, laminectomy and implantable prosthetics. As part of these surgical treatments, spinal constructs including vertebral rods are often used to provide stability to a treated region. Rods redirect stresses away from a damaged or defective region while healing takes place to restore proper alignment and generally support vertebral members. During surgical treatment, one or more rods and bone fasteners can be delivered to a surgical site. The rods may be attached via the fasteners to the exterior of two or more vertebral members. This disclosure describes an improvement over these prior technologies.

SUMMARY

In one embodiment, a spinal construct is provided. The spinal construct includes a coupling member including a first mating surface engageable with an existing fastener implant. The existing fastener implant is connected with an existing spinal rod implant. A connector is engageable with the existing fastener implant and has a rod extending therefrom. A locking member is engageable with a second mating surface of the coupling member. In some embodiments, systems, surgical instruments, implants and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
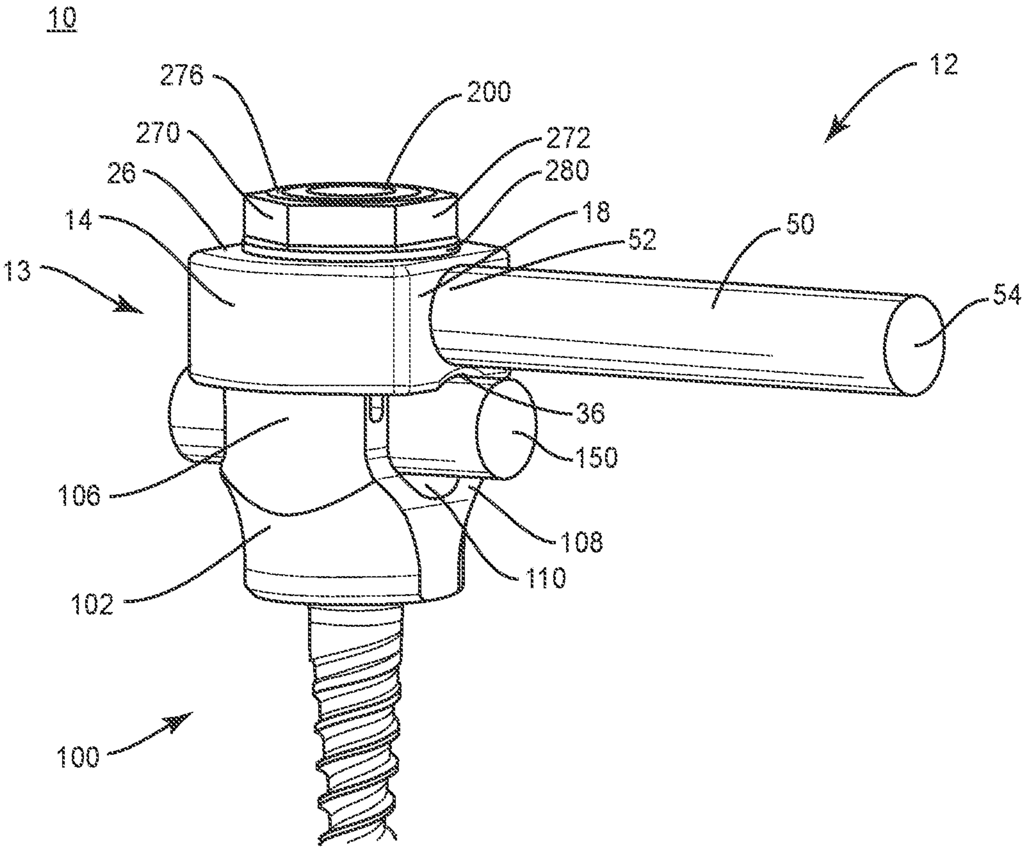
FIG. 1 is a perspective view of components of one embodiment of a system in accordance with the principles of the present disclosure.

The exemplary embodiments of the surgical system and related methods of use disclosed are discussed in terms of medical devices for the treatment of musculoskeletal disorders and more particularly, in terms of a surgical system and method for treatment of a spine disorder. In some embodiments, the systems and methods of the present disclosure are employed with a spinal joint fusion, for example, with a cervical, thoracic, lumbar and/or sacral region of a spine.

In some embodiments, the present surgical system includes a spinal construct comprising a connector. In some embodiments, the present surgical system includes a spinal construct comprising one or more revision minimally invasive surgical connectors. In some embodiments, the present surgical system includes a spinal construct that can be employed with a method for treating a spine with a plurality of spinal rods, which can be used to hold a spine until fusion occurs. In some embodiments, the present surgical system includes a spinal construct that can be employed with a method for treating a spine, which includes a pedicle subtraction osteotomy, a transforaminal lumbar interbody fusion (TLIF) and/or long constructs in heavy patients.

In some embodiments, the present surgical system includes a spinal construct comprising a bone screw and a spinal rod connector. In some embodiments, the present surgical system includes a spinal construct that can be employed with a method for treating a spine, which includes attaching a secondary rod to an existing pedicle screw. In some embodiments, the spinal construct includes a double-threaded setscrew (DTS), a connector and a nut, which allows the secondary rod to attach to the spinal construct. In some embodiments, a bottom thread of the DTS mates with the pedicle screw and allows it to function as the original setscrew. In some embodiments, the connector mates with the DTS and the pedicle screw head, and includes geometry to receive the secondary rod. In some embodiments, the nut threads onto a top thread of the DTS and clamps the connector to the top of the pedicle screw.

In some embodiments, the present surgical system includes a spinal construct that can be employed with a method for treating a spine, which includes connecting a second rod to a pedicle screw construct by changing the setscrew and installing the connector, which allows contouring the secondary rod independently of a primary rod.

In some embodiments, the spinal construct includes a connector comprising a joggle or offset with a secondary rod such that the secondary rod can be aligned with a primary rod. In some embodiments, the spinal construct comprises a pocket to fit to an existing MAS/fixed axial (FAS)/sagittal angulation (SAS) pedicle screw. In some embodiments, the spinal construct comprises a secondary rod that is integral to the connector.

In some embodiments, the spinal construct comprises an integral spinal rod and connector attachable to a fastener, such as a bone anchor or pedicle screw. In some embodiments, the spinal construct comprises a rod oriented in-line with an original/primary rod. In some embodiments, the spinal construct comprises a rod integral laterally or medially to a connector and allowing for the same functionality. In some embodiments, the spinal construct comprises a connector that adapts a fastener as a revision-ready implant. In some embodiments, the spinal construct comprises a one to two level extension of an existing implant.

In some embodiments, the spinal construct includes a primary rod disposed with a MAS, FAS or a SAS pedicle screw and a screw to rod connector. In some embodiments, a double-hex break-off nut and a double-thread setscrew connect the components. In some embodiments, the screw to rod connector comprises a secondary rod and setscrew receiver. In some embodiments, the nut clamps the rod-to-screw connector to the primary rod via the double-thread setscrew. In some embodiments, the bottom of the connector contacts the primary rod to distribute the load between the rod and the setscrew. In some embodiments, there is a gap between the double-threaded setscrew and the rod such that the double-threaded setscrew does not clamp the rod to the pedicle screw, however, the nut attaches the connector to the pedicle screw.

In some embodiments, the spinal construct comprises a flanged double-thread setscrew. In some embodiments, a top nut clamps the rod-to-screw connector to the flange on the setscrew via the top thread on the setscrew. In some embodiments, the load from the connector is distributed to the setscrew via the flange. In some embodiments, the rod-to-screw connector can rotate on the flange allowing the rods to be non-parallel.

In some embodiments, the spinal construct includes a revision connector configured to attach to one or more existing spinal constructs implanted with a body. In some embodiments, the spinal construct can be employed in a revision surgery to extend an existing screw and rod construct. In some embodiments, the spinal construct can be employed in a revision surgery to connect an existing spinal construct and extend the existing spinal construct to span one or more spinal levels.

In some embodiments, the present surgical system includes a spinal construct that can be employed in a revision surgery to connect to an existing rod implanted with a body. In some embodiments, the spinal construct and the existing spinal construct comprise an extension. In some embodiments, the present surgical system includes a spinal construct that can be employed in a revision surgery to connect to an existing bone screw and rod construct through a minimally invasive approach.

In some embodiments, one or all of the components of the surgical system may be disposable, peel-pack, pre-packed sterile devices. One or all of the components of the system may be reusable. The system may be configured as a kit with multiple sized and configured components.

In some embodiments, the surgical system of the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the surgical system of the present disclosure may be employed with other osteal and bone related applications, including those associated with diagnostics and therapeutics. In some embodiments, the disclosed surgical system may be alternatively employed in a surgical treatment with a patient in a prone or supine position, and/or employ various surgical approaches to the spine, including anterior, posterior, posterior mid-line, direct lateral, postero-lateral, and/or antero-lateral approaches, and in other body regions. The surgical system of the present disclosure may also be alternatively employed with procedures for treating the lumbar, cervical, thoracic, sacral and pelvic regions of a spinal column. The surgical system of the present disclosure may also be used on animals, bone models and other non-living substrates, such as, for example, in training, testing and demonstration.

The surgical system of the present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, microdiscectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. In some embodiments, as used in the specification and including the appended claims, the term "tissue" includes soft tissue, ligaments, tendons, cartilage and/or bone unless specifically referred to otherwise.

The following discussion includes a description of a surgical system including a spinal construct, related components and methods of employing the surgical system in accordance with the principles of the present disclosure. Alternate embodiments are also disclosed. Reference is made in detail to the exemplary embodiments of the present disclosure, which are illustrated in the accompanying figures. Turning to FIGS. 1-4, there are illustrated components of a surgical system, such as, for example, a spinal implant system 10.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, aluminum, commercially pure titanium, titanium alloys, Grade 5 titanium, super-elastic titanium alloys, cobaltchrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tricalcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or components of spinal constructs at a surgical site within a body of a patient, for example, a section of a spine. In some embodiments, one or more of the components of spinal implant system 10 are configured for engagement with existing constructs, which may include fastener implants and/or spinal rod implants attached with vertebrae in a revision surgery to manipulate tissue and/or correct a spinal disorder, as described herein. In some embodiments, one or more of the components of spinal implant system 10 can be employed in a revision surgery to connect an existing spinal construct and extend, revise or repair the existing spinal construct to span one or more spinal levels. Spinal implant system 10 comprises a spinal construct 12. In some embodiments, one or more components of spinal construct 12 are configured to extend an existing spinal rod implant with or without removing the existing rod implant. In some embodiments, existing spinal constructs may include one or more implants connected or fixed with tissue in a prior or different surgical procedure, separate in time and/or over a duration of time in the same surgical procedure.

Spinal construct 12 includes a connector 13. Connector 13 includes a body 14 that defines an axis X1. Body 14 includes walls 18, 20, 22, 24 that define a sleeve 33. Sleeve 33 extends between a surface 26 and a surface 28. In some embodiments, surfaces 26, 28 include a planar configuration and extend perpendicular to axis X1. Sleeve 33 defines an inner surface 30 that defines a cavity 32. Cavity 32 is configured for disposal of a receiver 102 of an existing fastener implant, such as, for example, a multi-axial fastener 100, as described herein. In some embodiments, the existing fastener implant may include sagittal angulation screws, pedicle screws, mono-axial screws, uni-planar screws, fixed screws, anchors, hooks, tissue penetrating screws, conventional screws, expanding screws, wedges, anchors, buttons, clips, snaps, friction fittings, compressive fittings, expanding rivets, staples, nails, adhesives, posts, connectors, fixation plates and/or posts.

Cavity 32 includes a substantially rectangular cross section. In some embodiments, cavity 32 may have various cross section configurations, such as, for example, oval, oblong, triangular, rectangular, square, polygonal, irregular, uniform, non-uniform, variable and/or tapered. In some embodiments, surface 30 may include gripping elements or surface 30 may be, for example, rough, arcuate, undulating, mesh, porous, semi-porous, dimpled and/or textured to facilitate engagement with fastener 100.

Figure 2:
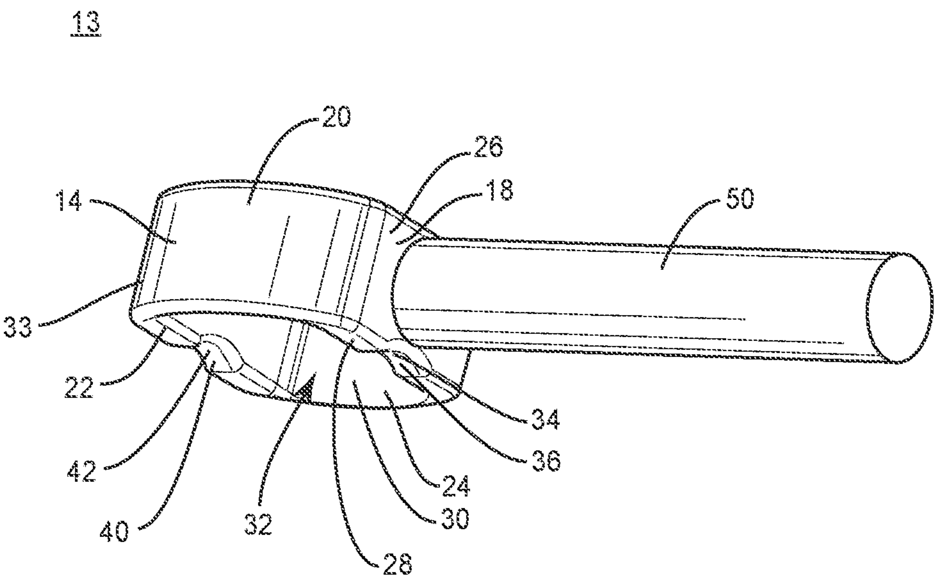
FIG. 2 is a perspective view of components of the system shown in FIG. 1.

A portion of surface 28 disposed along wall 18 defines a recess 36. In some embodiments, recess 36 includes a concave configuration, as shown in FIG. 2. Recess 36 is configured to conform to a shape of an existing implant, such as, for example, a spinal rod 150, as described herein. A portion of surface 28 disposed along wall 22 defines a recess 42. In some embodiments, recess 42 includes a concave configuration, as shown in FIG. 2. Recess 42 is configured to conform to the shape of spinal rod 150, as described herein. Recess 42 is disposed in alignment with recess 36 to facilitate disposal of spinal rod 150 with connector 13.

In some embodiments, wall 20 includes an arcuate surface configured for a mating engagement with an arm of receiver 102, as described herein. In some embodiments, wall 24 includes an arcuate surface configured for a mating engagement with an arm of receiver 102, as described herein.

Figure 3:
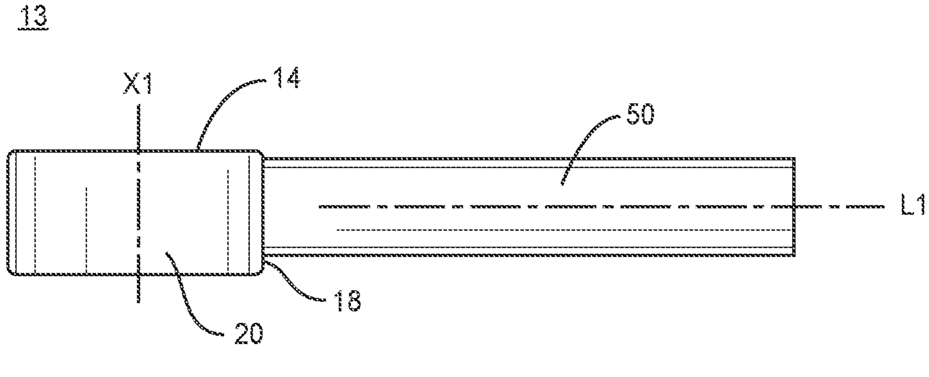
FIG. 3 is a side view of the components shown in FIG. 2.

A rod 50 extends from wall 18. Rod 50 defines an axis L1, as shown in FIG. 3. Rod 50 extends between an end 52 and an end 54. In some embodiments, rod 50 may have various cross section configurations, such as, for example, circular, oval, oblong, polygonal, irregular, uniform, non-uniform, variable, offset and/or tapered. End 54 is configured for connection with a receiver of one or a plurality of bone screws, as described herein.

In some embodiments, axis L1 is disposed perpendicular to axis X1. In some embodiments, all or a portion of rod 50 extends in the same plane as body 14. In some embodiments, all or a portion of rod 50 extends offset relative to body 14. In some embodiments, axis L1 may be disposed at alternate orientations relative to axis X1, such as, for example, transverse and/or other angular orientations such as acute or obtuse, coaxial and/or may be offset or staggered. In some embodiments, rod 50 is monolithically formed with body 14. In some embodiments, rod 50 may be integrally connected or include fastening elements and/or instruments for connection with body 14.

Figure 4:
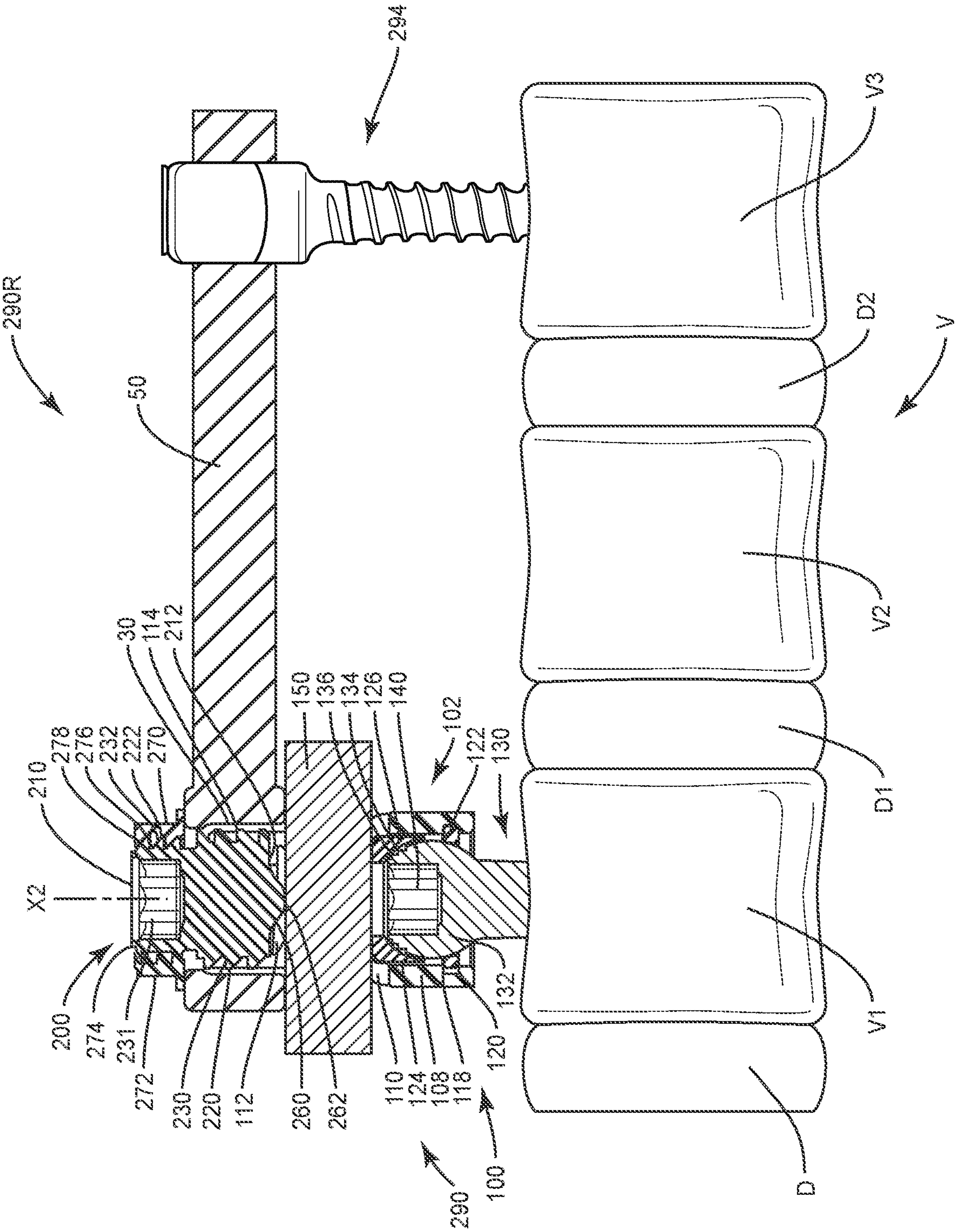
FIG. 4 is a cross section view of components of one embodiment of a system in accordance with the principles of the present disclosure disposed with vertebrae.

In some embodiments, rod 50 extends parallel to existing spinal rod implant 150, as shown in FIGS. 1 and 4. In some embodiments, connector 13 and rod 50 are configured to revise an existing spinal construct by extending an existing spinal rod 150 one or more spinal levels without removal of existing spinal rod 150 such that connector 13 allows for extension of rod 50 while providing clearance to accommodate existing spinal rod 150.

Fastener 100 includes receiver 102 that extends along and defines an axis X2. Receiver 102 includes a pair of spaced apart arms 106, 108 that define an implant cavity 110 therebetween configured for disposal of existing spinal rod implant 150. Arms 106, 108 each extend parallel to axis X2. In some embodiments, arm 106 and/or arm 108 may be disposed at alternate orientations, relative to axis X2, such as, for example, transverse, perpendicular and/or other angular orientations such as acute or obtuse, coaxial and/or may be offset or staggered. Arms 106, 108 each include an arcuate outer surface extending between a pair of side surfaces.

Cavity 110 is substantially U-shaped. In some embodiments, all or only a portion of cavity 110 may have alternate cross section configurations, such as, for example, closed, V-shaped, W-shaped, oval, oblong triangular, square, polygonal, irregular, uniform, non-uniform, offset, staggered, and/or tapered. Receiver 102 includes an inner surface 112. A portion of surface 112 includes a thread 114. Thread 114 includes a thread form that is configured for engagement with a coupling member, such as, for example, an existing set screw engaged with fastener 100 and existing spinal rod implant 150 and/or a set screw 200, as described herein, to retain existing spinal rod implant 150 within cavity 110 and connect connector 13 with fastener 100.

In some embodiments, surface 112 may be disposed with the coupling member in alternate fixation configurations, such as, for example, friction fit, pressure fit, locking protrusion/recess, locking keyway and/or adhesive. In some embodiments, all or only a portion of surface 112 may have alternate surface configurations to enhance engagement, such as, for example, rough, arcuate, undulating, mesh, porous, semi-porous, dimpled and/or textured.

In some embodiments, receiver 102 includes a surface 118 that defines a cavity, such as, for example, a groove 120 configured for disposal of a band, such as, for example, a C-shaped ring 122. Ring 122 is configured to engage an outer surface of a head 132 of shaft 130 and is disposable with groove 120 to resist and/or prevent axial translation of shaft 130 relative to receiver 102. In some embodiments, ring 122 is disposed within head 132 to enhance a retaining strength of fastener 100 and resist and/or prevent shearing of shaft 130. In some embodiments, surface 118 includes a cavity, such as, for example, a slot 124 configured to receive a flange of a part, such as, for example, a crown 126, as shown in FIG. 4.

Shaft 130 is configured to penetrate tissue, such as, for example, bone. Head 132 is engageable with receiver 102. Head 132 includes a substantially spherical proximal portion configured for moveable disposal with receiver 102 and crown 126. Head 132 includes a surface 134 that defines a plurality of ridges 136 to improve purchase of head 132 with crown 126. An engagement portion of crown 126 is concave or semi-spherical to accommodate the substantially spherical configuration of head 132 such that head 132 is rotatable relative to receiver 102.

Head 132 includes a socket 140 having a hexalobe geometry configured for disposal of a similarly shaped bit of a tool, such as, for example, a driver (not shown) to engage the driver with head 132 to rotate shaft 130. Socket 140 is in communication with cavity 110 such that a driver may be inserted between arms 106, 108 and translated axially, until the bit of the driver is disposed in socket 140. In some embodiments, socket 140 has a cruciform, phillips, square, hexagonal, polygonal, star cross sectional configuration configured for disposal of a correspondingly shaped portion of a driver.

Set screw 200 extends between an end 210 and an end 212. Set screw 200 includes a mating surface, such as, for example, a thread 220 and a mating surface, such as, for example, a thread 222. Thread 220 is configured for engagement with thread 114 of fastener 100. In some embodiments, thread 220 includes one or a plurality of threads configured for interlocking engagement with thread 114 of receiver 102, as described herein. In some embodiments, thread 220 is continuous along a portion of set screw 200. In some embodiments, thread 220 may include a single thread turn or a plurality of discrete threads. Thread 220 includes an external thread form 230.

Thread 222 is configured for engagement with a locking member, such as, for example, a nut 270 to fix connector 13 with fastener 100, as described herein. In some embodiments, thread 222 includes one or a plurality of threads configured for interlocking engagement with nut 270, as described herein. In some embodiments, thread 222 is continuous along a portion of setscrew 200. In some embodiments, thread 222 may include a single thread turn or a plurality of discrete threads. Thread 222 includes an external thread form 232. In some embodiments, thread 220 includes a buttress thread that resists and/or prevents pull out from fastener 100. In some embodiments, thread 222 includes a buttress thread that resists and/or prevents pull out from nut 270. In some embodiments, thread 220 is different relative to thread 222, and/or thread 220 defines a thread form that is different relative to a thread form defined by thread 222. In some embodiments, thread 220 and/or thread 222 defines a thread form, which may include, for example, ACME, ISO v-thread, square or a helical flange thread.

In some embodiments, set screw 200 includes a cavity 231 having a hexagonal cross-section configured to facilitate engagement with a surgical tool or instrument. In some embodiments, cavity 231 may have a cruciform, phillips, square, polygonal, hexalobular or star cross sectional configuration configured for disposal of a correspondingly shaped portion of a surgical tool or instrument.

In some embodiments, end 210 includes a break off portion (not shown). In some embodiments, the break off portion includes a tool engaging portion configured to engage a surgical tool or instrument (not shown). In some embodiments, the break off portion is frangibly connected to end 210. In some embodiments, the break off portion is fabricated from a fracturing and/or frangible material such that manipulation of the portion can fracture and separate the portion at a predetermined force and/or torque limit, as described herein. In some embodiments, as force and/or torque is applied to the break off portion and resistance increases, for example, due to fixation of threads 220, 222, as described herein, the predetermined torque and force limit is approached.

In some embodiments, the break off portion can fracture and separate at a predetermined force or torque limit. In some embodiments, the break off portion may be fabricated from a homogenous material or heterogeneously fabricated from different materials, and/or alternately formed of a material having a greater degree, characteristic or attribute of plastic deformability, frangible property and/or break away quality to facilitate fracture and separation of the portion. In some embodiments, the break off portion includes an inner diameter that facilitates a desired breakoff torque.

In some embodiments, end 212 includes a surface 260 that defines a protrusion 262. Protrusion 262 extends perpendicularly from surface 260 for engagement with existing spinal rod implant 150. In some embodiments, protrusion 262 may be disposed at alternate orientations, such as, for example, transverse and/or other angular orientations such as acute or obtuse, coaxial and/or may be offset or staggered. Protrusion 262 is configured to apply a force to existing spinal rod implant 150 to facilitate connection of connector 13 with fastener 100, as described herein.

Nut 270 includes a tool engaging surface 272 configured to engage a surgical tool or instrument (not shown), as described herein. In some embodiments, surface 272 includes a hexagonal cross-section to facilitate engagement with a surgical tool or instrument. In some embodiments, surface 272 may have alternative cross-sections, such as, for example, rectangular, polygonal, hexalobe, oval, or irregular. Nut 270 includes a surface 274 that defines a cavity 276. Surface 274 includes a thread form 278. Thread form 278 is configured for engagement with thread 222 of set screw 200, as described herein, to fix connector 13 with fastener 100 and existing spinal rod implant 150. In some embodiments, surface 272 may be disposed with set screw 200 in alternate fixation configurations, such as, for example, friction fit, pressure fit, locking protrusion/recess, locking keyway and/or adhesive. In some embodiments, all or only a portion of surface 272 may have alternate surface configurations to enhance engagement, such as, for example, rough, arcuate, undulating, mesh, porous, semi-porous, dimpled and/or textured. In some embodiments, nut 270 includes a circumferential flange 280 to facilitate the application of force to connector 13 and to facilitate fixation of one or more components of spinal construct 12. In some embodiments, nut 270 includes a break off portion or portion (not shown), similar to that described herein.

Set screw 200 is engageable with receiver 102 and nut 270 to fix connector 13 with fastener 100 to revise, repair and/or extend existing spinal rod implant 150. For example, thread 220 of set screw 200 is engaged with thread form 114 of receiver 102. Connector 13 is translated over receiver 102 such that sleeve 33 captures receiver 102. Nut 270 is engaged with thread 222 to fix connector 13 with fastener 100, as described herein. Nut 270 is configured to clamp connector 13 to fastener 100 via set screw 200. Nut 270 causes connector 13 to apply a force to fastener 100 and existing spinal rod implant 150 to fix connector 13 with fastener 100 to revise, repair and/or extend existing spinal rod implant 150. The force is distributed between nut 270, set screw 200, and surfaces 34, 40, as described herein.

In some embodiments, spinal implant system 10 can include one or a plurality of connectors 13 such as those described herein, which may be employed with a single vertebral level or a plurality of vertebral levels. In some embodiments, one or more connectors 13 may be engaged with vertebrae in various orientations, such as, for example, series, parallel, offset, staggered and/or alternate vertebral levels. In some embodiments, one or more connectors 13 may be employed with multi-axial screws, sagittal angulation screws, pedicle screws, mono-axial screws, uni-planar screws, fixed screws, anchors, hooks, tissue penetrating screws, conventional screws, expanding screws, wedges, anchors, buttons, clips, snaps, friction fittings, compressive fittings, expanding rivets, staples, nails, adhesives, posts, connectors, fixation plates and/or posts.

In assembly, operation and use, spinal implant system 10, similar to the systems and methods described herein, is employed with a surgical procedure, such as, for example, a surgical treatment of an applicable condition or injury of an affected section of a spinal column and adjacent areas within a body. In some embodiments, spinal implant system 10 includes connector 13, as described herein, which can be employed in a surgical treatment such as a revision surgery to revise, repair and/or extend an existing spinal construct. In some embodiments, spinal implant system 10 includes connector 13 employed in a revision surgery to connect with an existing spinal construct and extend the existing spinal construct to span one or more spinal levels. In some embodiments, the existing spinal construct may include one or more implants connected or fixed with tissue in a prior or different surgical procedure, separate in time and/or over a duration of time in the same surgical procedure. In some embodiments, during a surgical treatment, spinal implant system 10 may be completely or partially revised, removed or replaced.

For example, a surgical treatment may include adding length to an existing spinal construct 290 that includes fastener 100 and existing spinal rod implant 150, as shown in FIG. 4, implanted with vertebrae V in a prior surgical procedure and spans one or more intervertebral discs. In the prior surgical procedure, existing spinal rod implant 150 is implanted to structurally fuse adjacent vertebrae V1, V2 with existing spinal construct 290, which includes fastener 100 and existing spinal rod implant 150, to span intervertebral disc D. In one example, subsequent or different to the prior surgical procedure, an adjacent disc D1 develops a disorder for treatment. In some embodiments, the treatment of disc D1 includes connector 13 employed in a revision surgery to connect with spinal rod 150 to form a revised spinal construct 290R that extends to span spinal levels V1-V3, as described herein. In some embodiments, this configuration avoids disruption and tissue damage of the area of the prior surgical procedure, and reduction in healing and treatment duration.

In connection with the revision surgery, to treat a selected section of vertebrae V, including vertebrae V1, V2, V3, as shown in FIG. 4, a medical practitioner obtains access to a surgical site including vertebrae V in any appropriate manner, such as through incision and retraction of tissues. In some embodiments, spinal implant system 10 can be used in any surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway to access an existing spinal construct 290 including implanted fastener 100 and implanted existing spinal rod implant 150. The surgical pathway is utilized for implantation of components of spinal implant system 10. A preparation instrument (not shown) can be employed to prepare tissue surfaces of vertebrae V, as well as for aspiration and irrigation of a surgical region.

A set screw (not shown) that connected faster 100 and existing spinal rod implant 150 is removed from fastener 100. Set screw 200 is connected with a surgical instrument and delivered along the surgical pathway to engage fastener 100. Set screw 200 is rotated such that thread 220 engages thread form 114 of receiver 102 to fix set screw 200 with fastener 100. Connector 13 is translated over receiver 102 such that arms 106, 108 are captured by sleeve 33 within cavity 32. Connector 13 is moveable relative to fastener 100 and existing spinal rod implant 150 for orientation. Connector 13 is manipulated to dispose rod 50 in a position to extend existing spinal construct 290 to form a revised spinal construct 290R. Rod 50 is manipulated into a parallel orientation relative to spinal rod 150 for connection with bone screw 294, which is fastened with vertebrae V. Rod 50 extends existing spinal construct 290 one or more adjacent vertebral levels to form revised spinal construct 290R.

Nut 270 is translated into engagement with set screw 200 such that thread 220 engages thread form 278. Translation of nut 270 clamps connector 13 between existing spinal rod implant 150 and nut 270. Spinal construct 290R extends existing spinal construct 290, which spans disc D and vertebra V1, to span discs D1, D2 and vertebrae V2, V3, as shown in FIG. 4, without disruption of existing spinal construct 290. Spinal construct 290R is configured to structurally fuse adjacent vertebrae V2, V3. In some embodiments, rod 50 is configured to add support and strength to spinal implant system 10 along vertebrae V. In some embodiments, spinal construct 290R is adjustable to selectively span one or more vertebrae.

Upon completion of the procedure, the surgical instruments, assemblies and non-implanted components of spinal implant system 10 are removed from the surgical site and the incision is closed. One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of the bone fasteners with vertebrae. In some embodiments, the agent may include one or a plurality of therapeutic agents and/or pharmacological agents for release, including sustained release, to treat, for example, pain, inflammation and degeneration.

Figure 5:
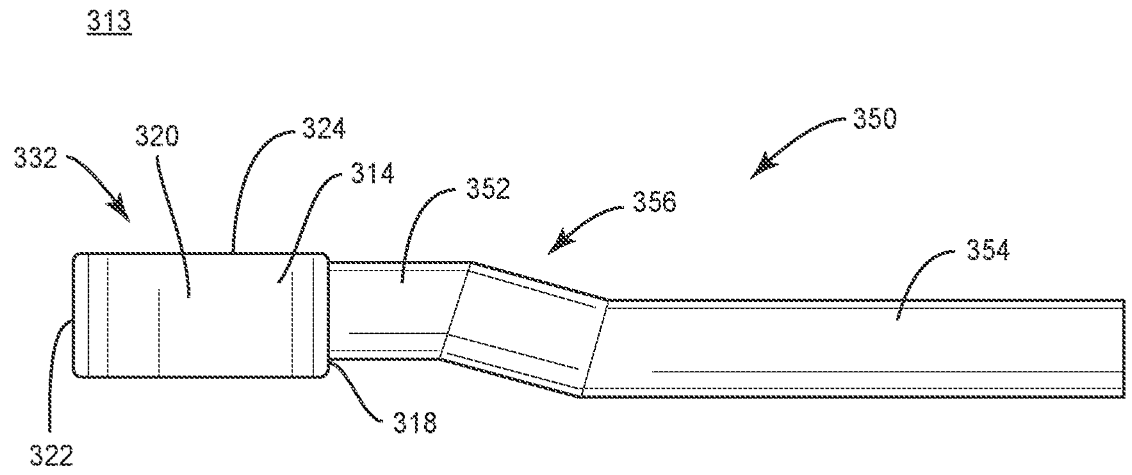
FIG. 5 is a side view of components of one embodiment of a system in accordance with the principles of the present disclosure.
Figure 6:
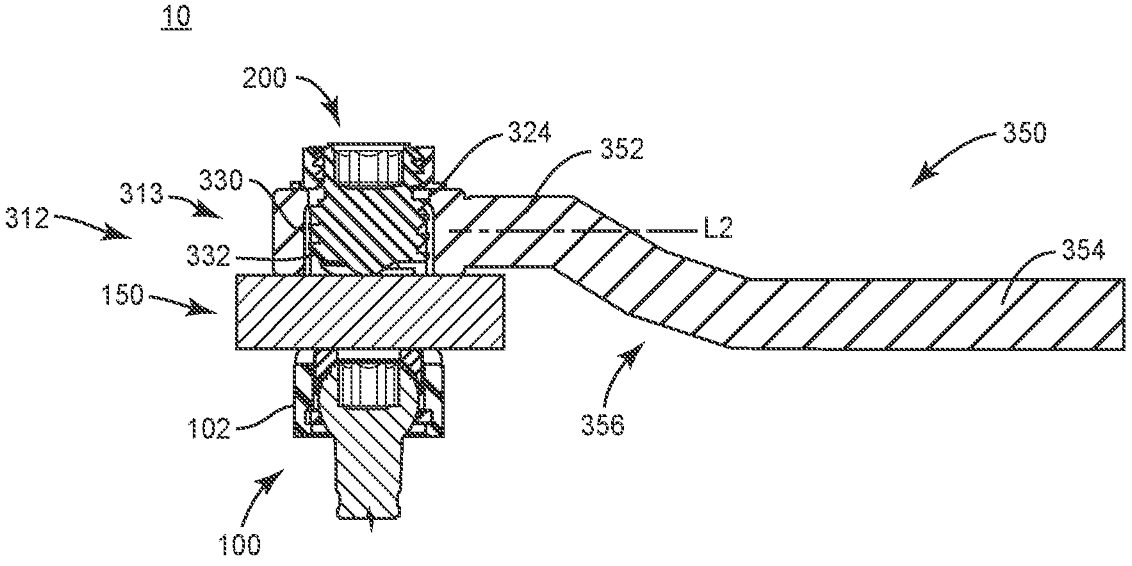
FIG. 6 is a cross section view of components of one embodiment of a system in accordance with the principles of the present disclosure.
Figure 7:
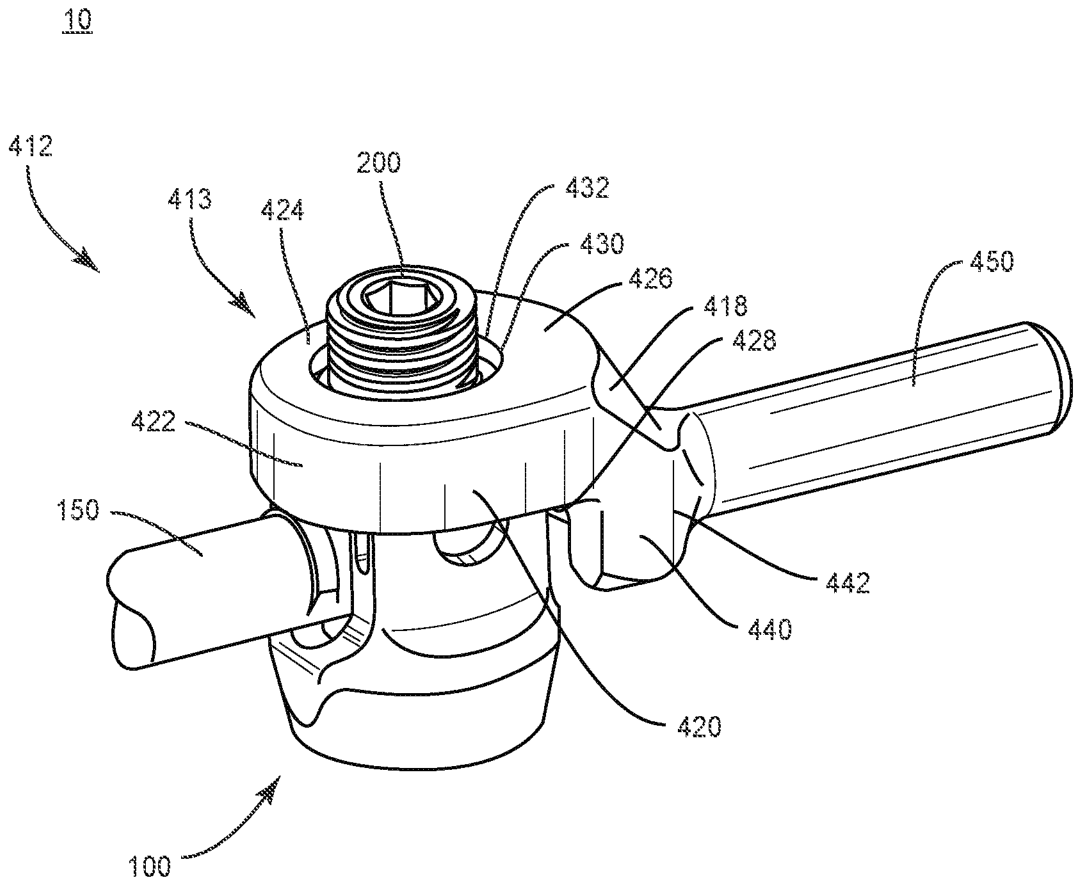
FIG. 7 is a break away perspective view of components of one embodiment of a system in accordance with the principles of the present disclosure.

In one embodiment, as shown in FIGS. 5 and 6, spinal implant system 10, similar to the systems and methods described herein, includes a spinal construct 312 that includes a connector 313, similar to connector 13 described herein. Spinal construct 312 can be employed with an existing spinal construct, similar to that described herein, for example, spinal construct 290 including faster 100 and existing spinal rod implant 150, as described herein.

Connector 313 includes a body 314, similar to body 14 described herein. Body 314 includes walls 318, 320, 322, 324 that define a sleeve 333. Sleeve 333 defines a cavity 332, similar to cavity 32 described herein. A rod 350, similar to rod 50 described herein, extends from wall 318. Rod 350 includes a shaft 352 and a shaft 354. Shaft 352 extends along an axis L2. Rod 350 includes an offset 356 such that rod 350 can be aligned with existing spinal rod implant 150. In some embodiments, offset 356 comprises a joggle relative to axis L2. In some embodiments, rod 350 includes offset 356 such that shaft 354 is co-axial with existing spinal rod implant 150, as shown in FIG. 6. In some embodiments, connector 313 and rod 350 are configured to repair and/or revise spinal construct 312 by extending existing spinal rod 150 one or more spinal levels without removal of existing spinal rod 150 such that connector 313 allows for clearance and housing of existing spinal rod 150, as described herein.

Set screw 200 and nut 270, as described herein, fix connector 313 with fastener 100 and existing spinal rod implant 150. Nut 270 is configured to clamp connector 313 to fastener 100 via set screw 200. Nut 270 causes connector 313 to apply a force to fastener 100 and existing spinal rod implant 150. The force is distributed between nut 270, set screw 200 and the recesses of connector 313, similar to that described herein.

In one embodiment, as shown in FIGS. 7-12, spinal implant system 10, similar to the systems and methods described herein, includes a spinal construct 412 including a connector 413, similar to connector 13 described herein, which can be employed with an existing spinal construct, similar to that described herein.

Connector 413 includes a body 414, similar to body 14 described herein. Body 414 includes a wall 418 and a wall 420 having an arcuate configuration. Walls 418, 420 define a sleeve 433, similar to sleeve 33 described herein. Sleeve 433 extends between a surface 426 and a surface 428. In some embodiments, surfaces 426, 428 include a planar configuration. Walls 418, 420 include an inner surface 430 that defines a cavity 432, similar to cavity 32 described herein.

Wall 418 includes an extension 440. Extension 440 extends from surface 428. In some embodiments, extension 440 extends perpendicular to surface 428. In some embodiments, extension 440 may be disposed at alternate orientations, relative to surface 428, such as, for example, transverse, and/or other angular orientations such as acute or obtuse, coaxial and/or may be offset or staggered. Extension 440 includes an offset 442, which is offset and/or angled to provide a low profile spinal construct 412.

A rod 450, similar to rod 50 described herein, extends from surface 442. Extension 440 is disposed in a position to orient rod 450 in a configuration to repair and/or revise an existing spinal construct by extending existing spinal rod 150 one or more spinal levels without removal of existing spinal rod 150 such that connector 413 allows for clearance and housing of existing fastener 100 and/or spinal rod 150, as described herein and shown in FIG. 7. In some embodiments, connector 413 is configured to provide a sagittal offset of rod 450. In some embodiments, connector 413 is configured for rotation in a plane of a patient body, such as, for example, a coronal plane to accommodate placement of revision spinal construct.

In assembly, operation and use, spinal implant system 10, similar to the systems and methods described herein, includes connector 413, as described herein, which can be employed in a surgical treatment such as a revision surgery to revise, repair and/or extend an existing spinal construct. In some embodiments, spinal implant system 10 includes connector 413 employed in a revision surgery to connect with an existing spinal construct and extend the existing spinal construct to span one or more spinal levels. In some embodiments, the existing spinal construct may include one or more implants connected or fixed with tissue in a prior or different surgical procedure, separate in time and/or over a duration of time in the same surgical procedure.

Figure 8:
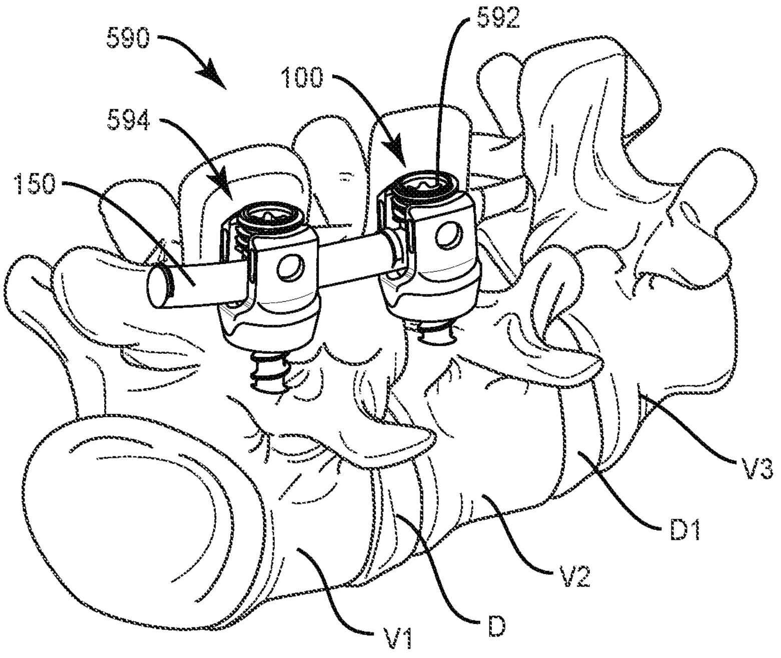
FIG. 8 is a perspective view of components of one embodiment of a system in accordance with the principles of the present disclosure disposed with vertebrae.

For example, a surgical treatment may include adding length to an existing spinal construct 590 that includes fastener 100 and existing spinal rod implant 150, as shown in FIG. 8, implanted with vertebrae V in a prior surgical procedure and spans one or more intervertebral discs. In the prior surgical procedure, existing spinal rod implant 150 is implanted to structurally fuse adjacent vertebrae V1, V2 with existing spinal construct 590, which includes fastener 100 and existing spinal rod implant 150, to span intervertebral disc D. In one example, subsequent or different to the prior surgical procedure, an adjacent disc D1 develops a disorder for treatment. In some embodiments, the treatment of disc D1 includes connector 413 employed in a revision surgery to connect with existing spinal rod implant 150 to form a revised spinal construct 590R that extends to span spinal levels V1-V3, as described herein. In some embodiments, this configuration avoids disruption and tissue damage of the area of the prior surgical procedure, and reduction in healing and treatment duration.

In connection with the revision surgery, to treat a selected section of vertebrae V, including vertebrae V1, V2, V3, a medical practitioner obtains access to a surgical site including vertebrae V in any appropriate manner, such as through incision and retraction of tissues. In some embodiments, spinal implant system 10 can be used in any surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway to access an existing spinal construct 590 including implanted fastener 100 and implanted existing spinal rod implant 150. The surgical pathway is utilized for implantation of components of spinal implant system 10. A preparation instrument (not shown) can be employed to prepare tissue surfaces of vertebrae V, as well as for aspiration and irrigation of a surgical region.

Figure 9:
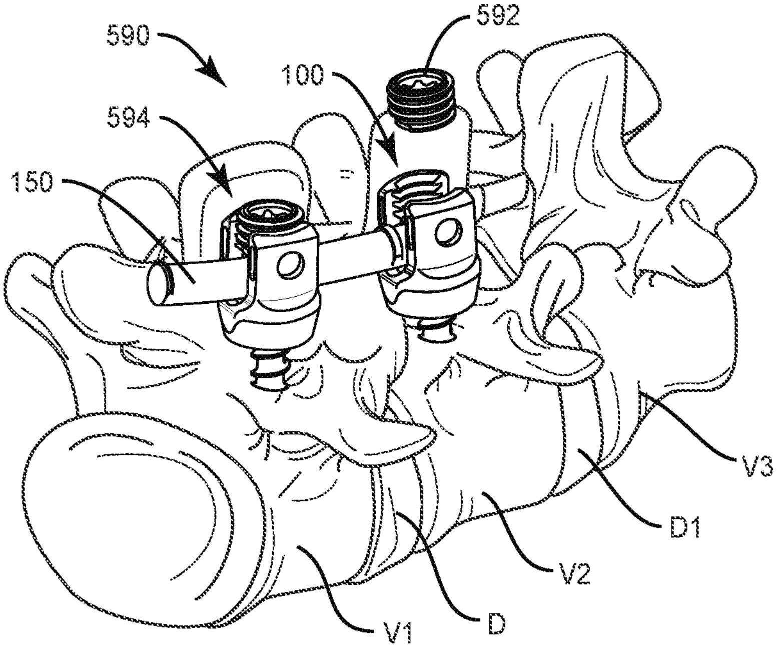
FIG. 9 is a perspective view of the components and vertebrae shown in FIG. 8.
Figure 10:
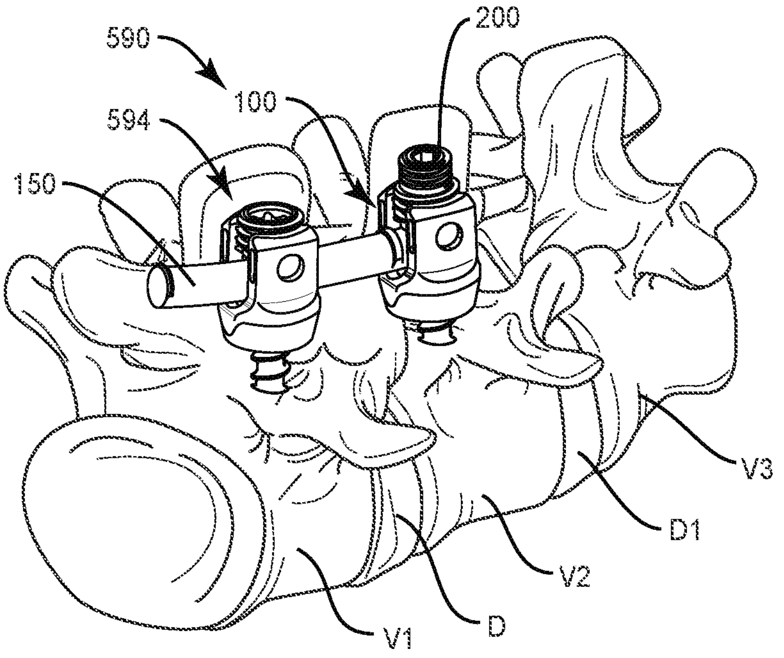
FIG. 10 is a perspective view of components of one embodiment of a system in accordance with the principles of the present disclosure disposed with vertebrae.
Figure 11:
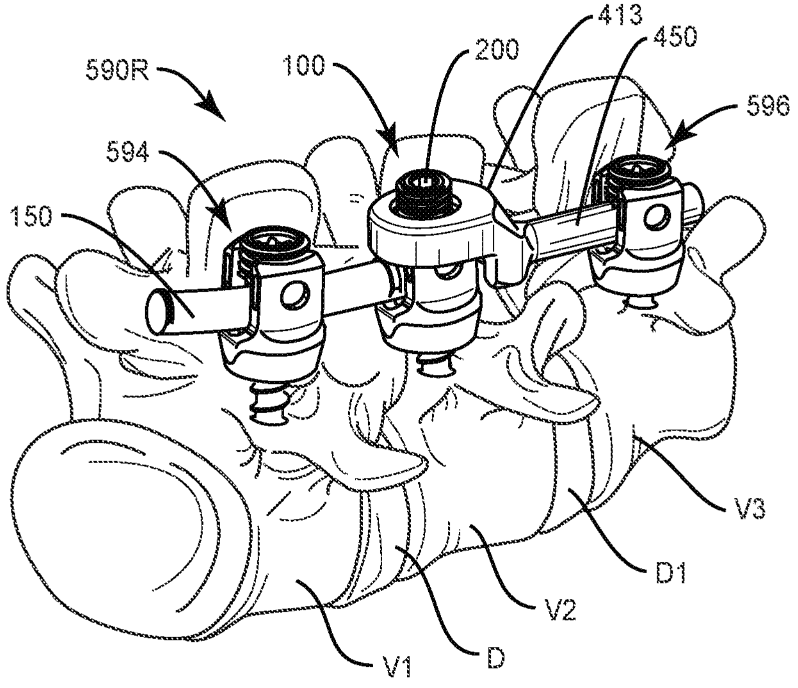
FIG. 11 is a perspective view of components of one embodiment of a system in accordance with the principles of the present disclosure disposed with vertebrae.

A set screw 592 that connected fastener 100 and existing spinal rod implant 150 is removed from fastener 100, as shown in FIG. 9. Set screw 200 is connected with a surgical instrument and delivered along the surgical pathway to engage fastener 100, as shown in FIG. 10. Set screw 200 is rotated such that thread 220 engages thread form 114 of receiver 102 to fix set screw 200 with fastener 100. Connector 413 is translated over receiver 102 such that arms 106, 108 are captured by sleeve 433 within cavity 432, as shown in FIG. 11. Connector 413 is moveable relative to fastener 100 and existing spinal rod implant 150 for orientation. Connector 413 is manipulated to dispose rod 450 in a position to extend existing spinal construct 590 to form a revised spinal construct 590R. Rod 450 is manipulated into a coaxial orientation relative to existing spinal rod implant 150 for connection with bone screw 596, which is fastened with vertebra V3. Rod 450 extends existing spinal construct 590 one or more adjacent vertebral levels to form revised spinal construct 590R.

Figure 12:
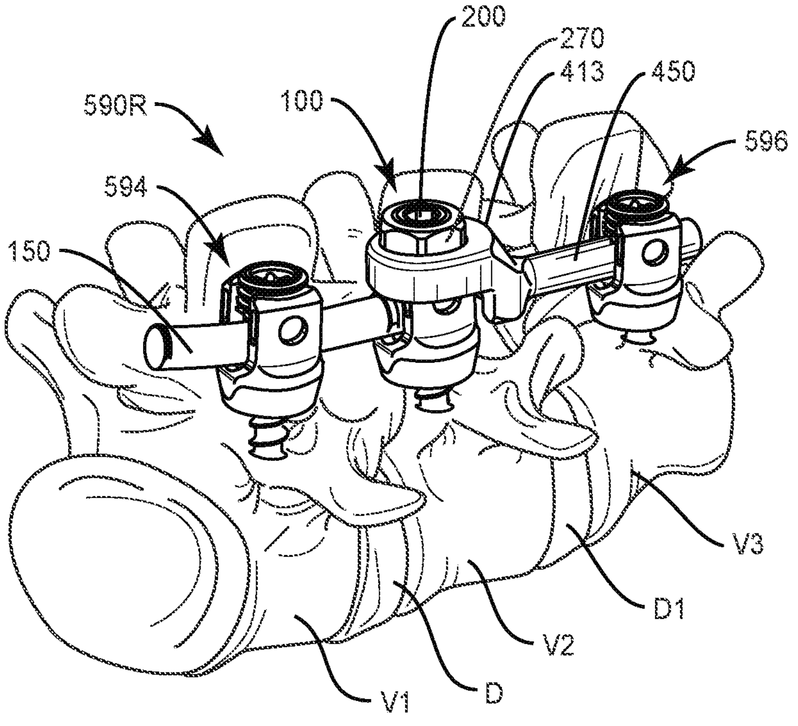
FIG. 12 is a perspective view of components of one embodiment of a system in accordance with the principles of the present disclosure disposed with vertebrae.

Nut 270 is translated into engagement with set screw 200 such that thread 222 engages thread form 278, as shown in FIG. 12. Translation of nut 270 clamps connector 413 between existing spinal rod implant 150 and nut 270. Spinal construct 590R extends existing spinal construct 590, which spans disc D and vertebra V1, to span disc D1 and vertebrae V2, V3, as shown in FIG. 12, without disruption of existing spinal construct 590. Spinal construct 590R is configured to structurally fuse adjacent vertebrae V2, V3. In some embodiments, rod 450 is configured to add support and strength to spinal implant system 10 along vertebrae V. In some embodiments, spinal construct 590R is adjustable to selectively span one or more vertebrae. In one embodiment, as shown in FIGS. 13-20, spinal implant system 10, similar to the systems and methods described herein, includes a spinal construct 690 that includes a connector 413, as described herein with regard to FIGS. 7-12, which can be employed with an existing spinal construct 690, similar to that described herein.

Figure 13:
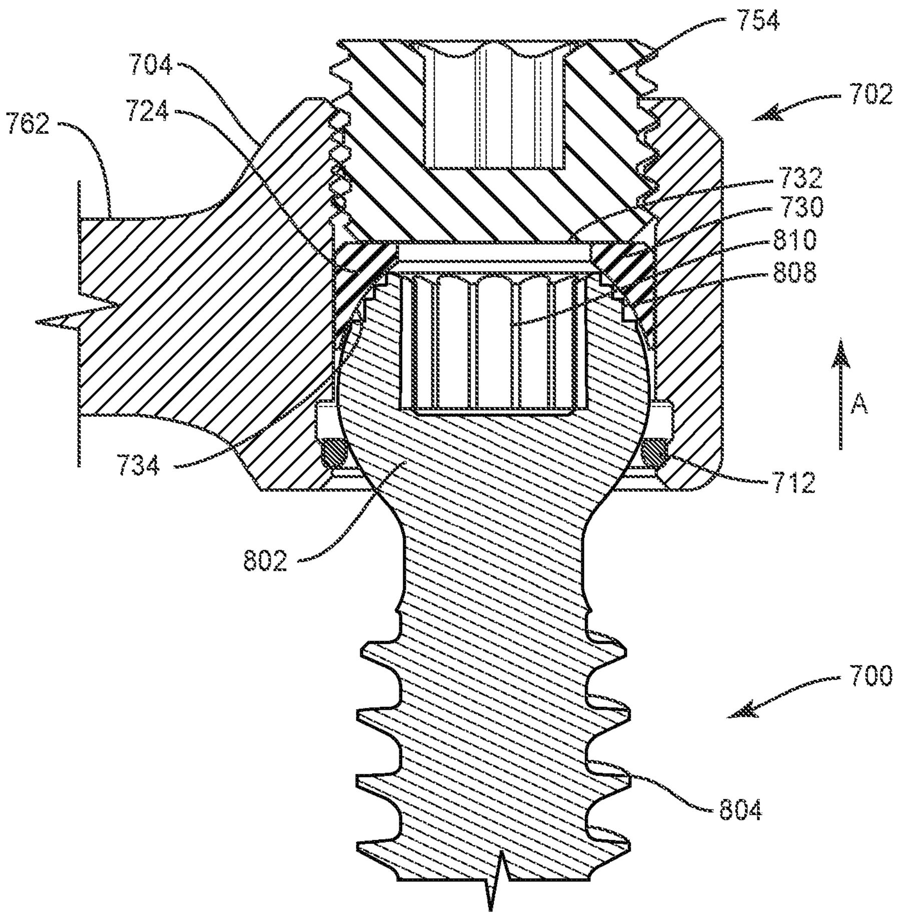
FIG. 13 is a cross section view of components of one embodiment of a system in accordance with the principles of the present disclosure.
Figure 14:
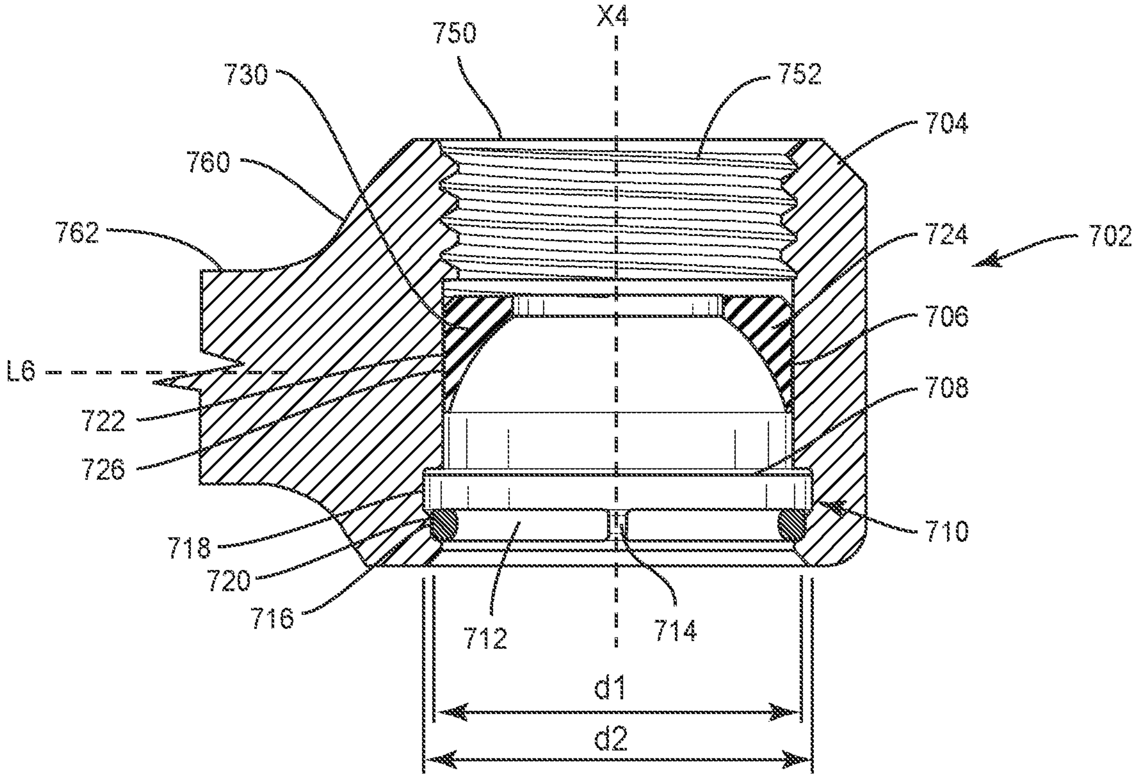
FIG. 14 is a cross section view of components of one embodiment of a system in accordance with the principles of the present disclosure.

Spinal construct 690 includes a fastener, such as, for example, a bone screw 700 connectable with a member, such as, for example, a receiver 702, as shown in FIGS. 13 and 14. Screw receiver 702 includes a wall 704 that defines a sleeve 705. Wall 704 includes an inner surface 706 that defines a cavity 708. Cavity 708 is configured for disposal of a head 802 of bone screw 700, as described herein. Sleeve 705 extends along an axis X4. In some embodiments, sleeve 705 may extend in alternate configurations relative to axis X4, such as, for example, arcuate, offset, staggered and/or angled portions. Cavity 708 is substantially circular. In some embodiments, all or only a portion of cavity 708 may have alternate cross section configurations, such as, for example, closed, V-shaped, W-shaped, oval, U-shaped, oblong, polygonal, irregular, uniform, non-uniform, offset, staggered, and/or tapered. In some embodiments, spinal construct 690 may include one or a plurality of receivers 702.

Surface 706 defines a groove 710 configured for disposal of a band, such as, for example, a circumferential ring 712. Ring 712 includes a circumference that extends between ends defining an opening, such as, for example, a gap 714, which facilitates expansion and contraction. Groove 710 includes a portion, such as for, example, a circumferential channel 716 having a diameter d1 and a portion, such as for, example, a circumferential channel 718 having a diameter d2. In some embodiments, diameter d2 is greater than diameter d1.

Channel 716 is disposed adjacent and proximal to channel 718. Channel 718 is separate from channel 716 by a protrusion, such as, for example, a lip 720. In some embodiments, bone screw 700 is manually engageable with receiver 702 and/or bone screw 700 is coupled with receiver 702 in a non-instrumented assembly such that ring 712 translates from and into channels 716, 718, and over lip 720, as described herein. Ring 712 is expandable and resilient between a contracted and/or capture orientation and an expanded orientation, as described herein. In some embodiments, ring 712 facilitates manual engagement of receiver 702 and bone screw 700 such that receiver 702 is attached with bone screw 700 in a non-instrumented assembly, as described herein.

In some embodiments, wall 704 defines a slot 722 configured for disposal of a part, such as, for example, a crown 724, as described herein. Slot 722 is defined by a surface 726 of wall 704. In some embodiments, all or only a portion of surface 726 may have alternate surface configurations to enhance engagement with crown 724, such as, for example, rough, arcuate, undulating, mesh, porous, semiporous, dimpled and/or textured.

Crown 724 includes a wall 730 having an end surface 732 and an end surface 734. Surface 732 is configured for engagement with a coupling member, as described herein. Surface 734 defines a curved portion of crown 724 engageable with bone screw 700, as described herein. In some embodiments, all or only a portion of surface 734 may have alternate cross section configurations, such as, for example, oval, oblong, polygonal, irregular, uniform, non-uniform, offset, staggered, and/or tapered.

Receiver 702 includes an inner surface 750. A portion of surface 750 includes a thread form 752. Thread form 752 is configured for engagement with a coupling member, as described herein. Receiver 702 includes an outer surface 760. An existing spinal rod implant 762 extends from surface 760 along an axis L6. Existing spinal rod implant 762 extends transverse to axis X4. In some embodiments, existing spinal rod implant 762 may extend in alternate orientations relative to axis X4, such as, for example, arcuate, tapered, perpendicular, parallel and/or other angular orientations such as acute or obtuse, co-axial and/or may be offset or staggered. Existing spinal rod implant 762 extends between an end 764 and an end 766. In some embodiments, existing spinal rod implant 762 may have various cross section configurations, such as, for example, circular, oval, oblong, polygonal, irregular, uniform, non-uniform, variable, offset and/or tapered. End 766 is configured for connection with a receiver of one or a plurality of bone fasteners, as described herein.

In some embodiments, existing spinal rod implant 762 is monolithically formed with receiver 702. In some embodiments, existing spinal rod implant 762 is integrally connected with receiver 702 by welding. In some embodiments, existing spinal rod implant 762 is integrally connected with receiver 702 by fastening elements and/or instruments to facilitate connection.

Bone screw 700 includes head 802 and a shaft 804. Head 802 includes a surface 806 that defines a plurality of ridges 808 to improve purchase of head 802 with crown 724. Head 802 includes a tool engaging portion 810 configured to engage a surgical tool or instrument, as described herein. In some embodiments, portion 810 includes a hexagonal cross-section to facilitate engagement with a surgical tool or instrument, as described herein. In some embodiments, portion 810 may have alternative cross-sections, such as, for example, rectangular, polygonal, hexalobe, oval, or irregular. Shaft 804 is configured to penetrate tissue, such as, for example, bone. In some embodiments, shaft 804 includes an outer surface having an external thread form. In some embodiments, the external thread form may include a single thread turn or a plurality of discrete threads.

In some embodiments, receiver 702 is manually engageable with head 802 in a non-instrumented assembly such that ring 712 translates from disposal with channel 716 and into channel 718, as described herein. In some embodiments, manual engagement and/or non-instrumented assembly of receiver 702 and head 802 includes coupling without use of separate and/or independent instrumentation engaged with the components to effect assembly. In some embodiments, manual engagement and/or non-instrumented assembly includes a practitioner, surgeon and/or medical staff grasping receiver 702 and bone screw 700 and forcibly assembling the components. In some embodiments, manual engagement and/or non-instrumented assembly includes a practitioner, surgeon and/or medical staff grasping receiver 702 and bone screw 700 and forcibly snap fitting the components together, as described herein. In some embodiments, manual engagement and/or non-instrumented assembly includes a practitioner, surgeon and/or medical staff grasping receiver 702 and bone screw 700 and forcibly pop fitting the components together and/or pop fitting receiver 702 onto bone screw 700, as described herein. In some embodiments, a force is required to manually engage receiver 702 and bone screw 700 and forcibly assemble the components.

Figure 15:
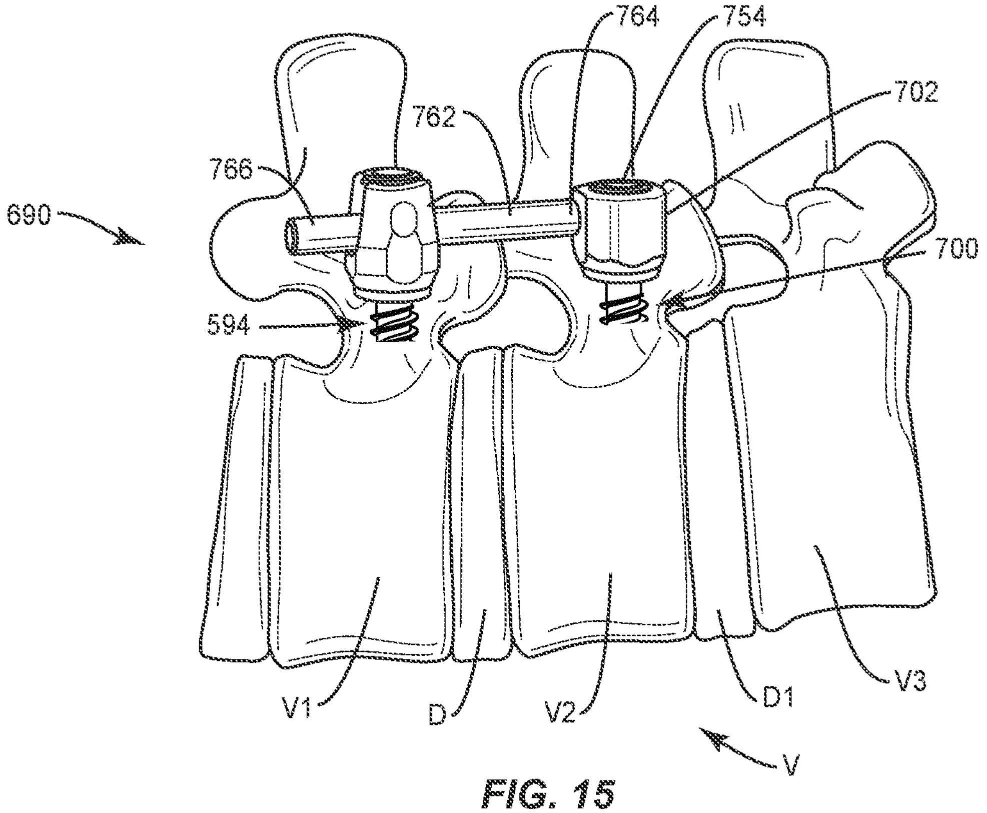
FIG. 15 is a perspective view of components of one embodiment of a system in accordance with the principles of the present disclosure.

In assembly, operation and use, spinal implant system 10, similar to the systems and methods described herein, includes connector 413, as described herein, which is employed in a surgical treatment including a revision surgery to revise, repair and/or extend an existing spinal construct 690 that includes bone screw 700 and existing spinal rod implant 762, as shown in FIG. 15, implanted with vertebrae V in a prior surgical procedure and spans one or more intervertebral discs. In the prior surgical procedure, existing spinal rod implant 762 is implanted spanning a single vertebral disc D to structurally fuse adjacent vertebrae V1, V2 with existing spinal construct 690. In one example, subsequent or different to the prior surgical procedure, an adjacent disc D1 develops a disorder for treatment. In some embodiments, the treatment of disc D1 includes connector 413 employed in a revision surgery to connect with existing spinal rod implant 762 to form a revised spinal construct 690R that extends to span spinal levels V1-V3, as described herein. In some embodiments, this configuration avoids disruption and tissue damage of the area of the prior surgical procedure, and reduction in healing and treatment duration.

In connection with the revision surgery, to treat a selected section of vertebrae V, including vertebrae V1, V2, V3, a medical practitioner obtains access to a surgical site including vertebrae V in any appropriate manner, such as through incision and retraction of tissues. In some embodiments, spinal implant system 10 can be used in any surgical method or technique including open surgery, mini-open surgery, minimally invasive surgery and percutaneous surgical implantation, whereby vertebrae V is accessed through a mini-incision, or a sleeve that provides a protected passageway to the area. Once access to the surgical site is obtained, the particular surgical procedure can be performed for treating the spine disorder.

An incision is made in the body of a patient and a cutting instrument (not shown) creates a surgical pathway to access existing spinal construct 690 including implanted bone screw 700 and implanted existing spinal rod implant 762. The surgical pathway is utilized for implantation of components of spinal implant system 10. A preparation instrument (not shown) can be employed to prepare tissue surfaces of vertebrae V, as well as for aspiration and irrigation of a surgical region.

Figure 16:
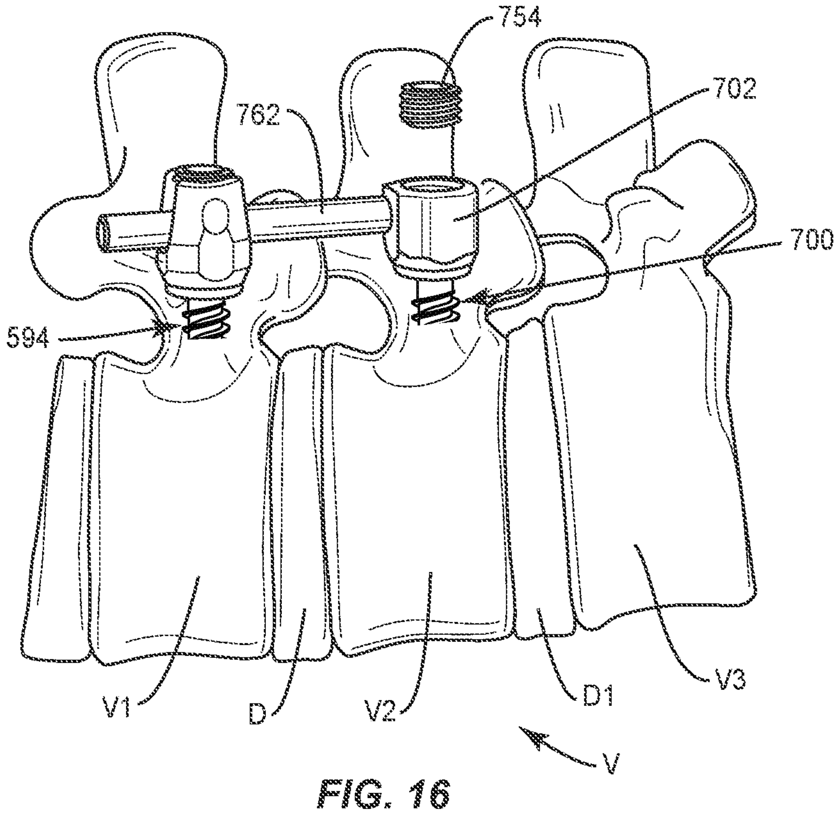
FIG. 16 is a perspective view of components of one embodiment of a system in accordance with the principles of the present disclosure.
Figure 17:
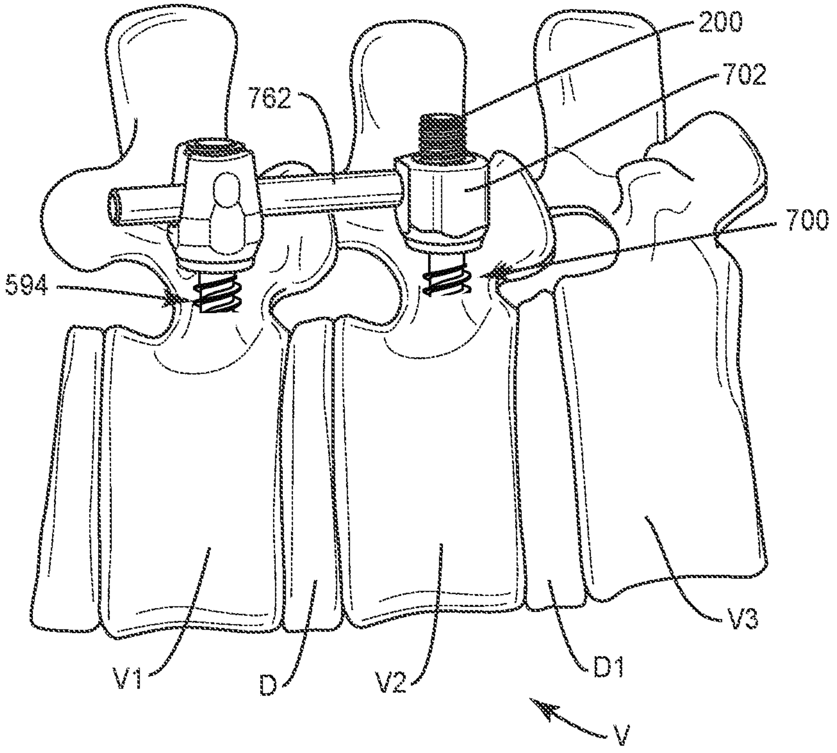
FIG. 17 is a perspective view of components of one embodiment of a system in accordance with the principles of the present disclosure.
Figure 18:
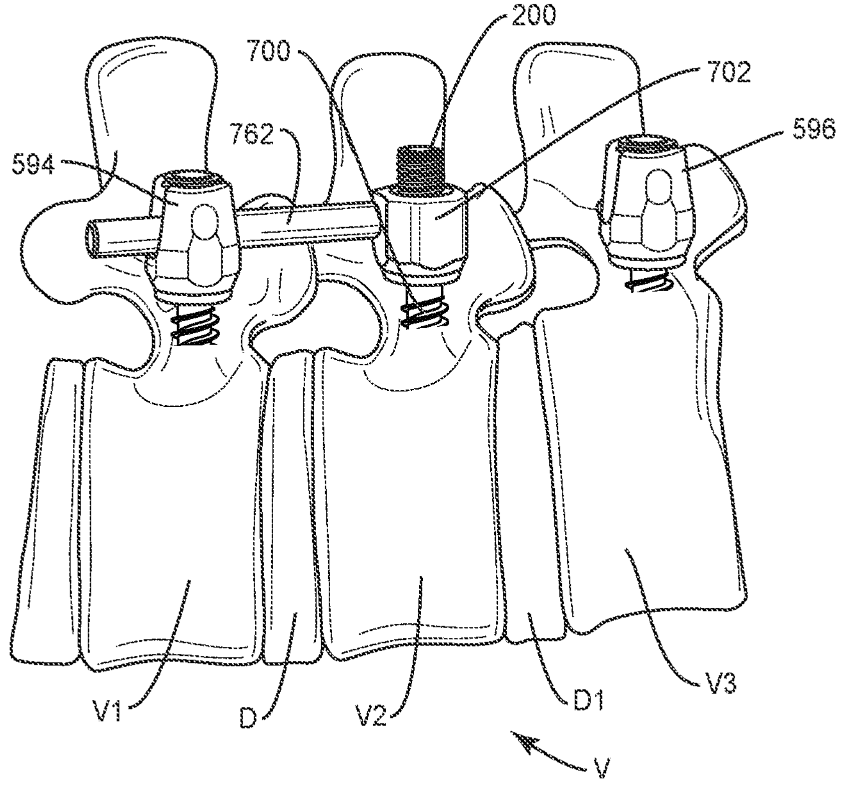
FIG. 18 is a perspective view of components of one embodiment of a system in accordance with the principles of the present disclosure.
Figure 19:
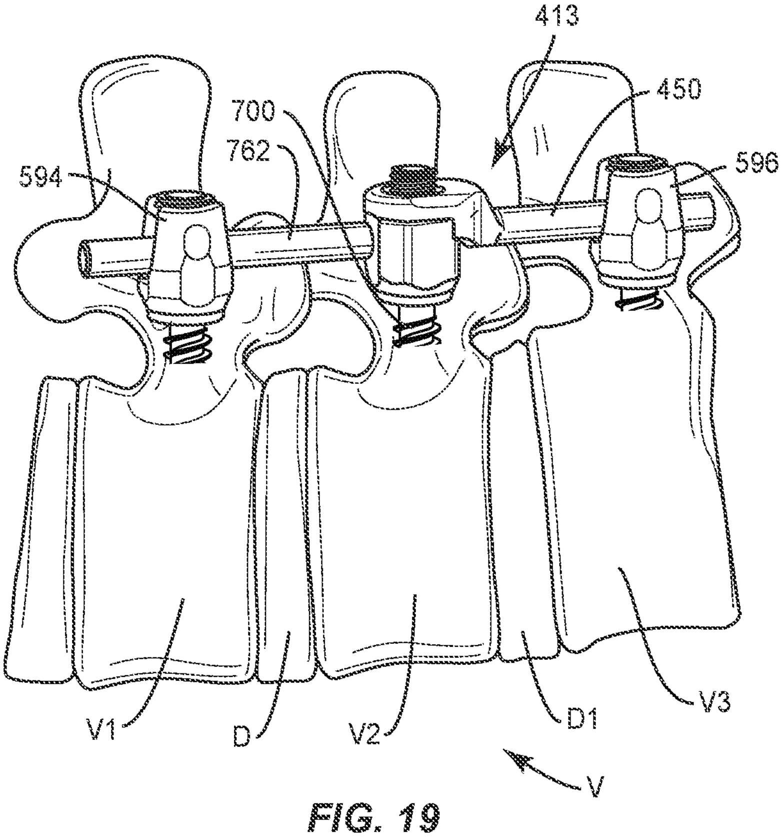
FIG. 19 is a perspective view of components of one embodiment of a system in accordance with the principles of the present disclosure.

A set screw 754 that fixed bone screw 700 and existing spinal rod implant 762 is removed from bone screw 700, as shown in FIG. 16. Set screw 200 is connected with a surgical instrument and delivered along the surgical pathway to engage bone screw 700, as shown in FIG. 17. Set screw 200 is rotated such that thread 220 engages thread form 752 of receiver 702 to fix set screw 200 with bone screw 700. Connector 413 is translated over receiver 702 such that receiver 702 is captured by sleeve 433 within cavity 432, as shown in FIGS. 18 and 19. Connector 413 is moveable relative to bone screw 700 and existing spinal rod implant 762 for orientation. Connector 413 is manipulated to dispose rod 450 in a position to extend existing spinal construct 690 to form a revised spinal construct 690R. In some embodiments, rod 450 is manipulated into a coaxial orientation relative to spinal rod 762 for connection with bone screw 596, which is fastened with vertebrae V. Rod 450 extends existing spinal construct 690 one or more adjacent vertebral levels to form revised spinal construct 690R.

Figure 20:
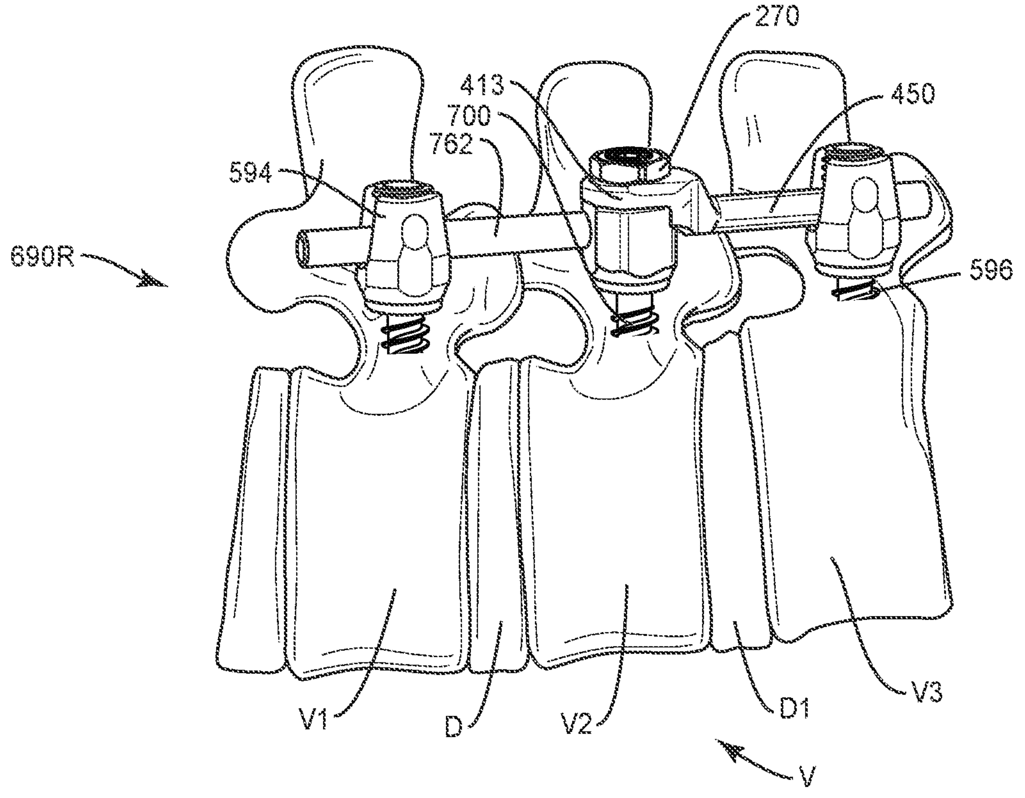
FIG. 20 is a perspective view of components of one embodiment of a system in accordance with the principles of the present disclosure.

Nut 270 is translated into engagement with set screw 200 such that thread 222 engages thread form 278, as shown in FIG. 20. Translation of nut 270 clamps connector 413 between existing spinal rod implant 762 and nut 270. Spinal construct 690R extends existing spinal construct 690, which spans disc D and vertebra V1, to span disc D1 and vertebrae V2, V3, without disruption of existing spinal construct 690. Spinal construct 690R is configured to structurally fuse adjacent vertebrae V2, V3. In some embodiments, rod 450 is configured to add support and strength to spinal implant system 10 along vertebrae V. In some embodiments, spinal construct 690R is adjustable to selectively span one or more vertebrae.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A kit for spinal revision surgery, the kit comprising:

a first implant and;

one or more coupling members each including a first thread and a second thread, the first thread being configured for engagement with a thread of a receiver of the first implant, the first implant having a first spinal rod at least partially disposed in the receiver;

one or more connectors each comprising a body, the body defining an aperture configured for disposal of one of the coupling members, the body comprising opposite inner and outer surfaces, the inner surface defining a cavity configured for disposal of the receiver, the one or more connectors each comprising a second spinal rod extending from the outer surface; and one or more locking members each configured for engagement with the second thread of the one or more coupling members, a crown being positioned in a cavity of the receiver in supporting relation to the first spinal rod;

the first implant further comprising a bone fastener;

a posterior edge of the second spinal rod being substantially coplanar with a posterior end of the first thread along a plane which is normal to a first axis that is substantially transverse to a second axis defined along a length of the second spinal rod;

wherein the first spinal rod of the first implant and the second spinal rod are disposed in a spaced apart relation to one another along the first axis.

2. The kit recited in claim 1, wherein the first axis is substantially transverse to a third axis defined along a length of the first spinal rod.

3. The kit recited in claim 1, wherein the bone fastener includes the receiver, a head, the crown and a band, the head and the crown being positioned in the cavity of the receiver, the band being positioned in a groove such that the band directly engages the head of the bone fastener.

4. The kit recited in claim 1, wherein the one or more connectors each comprises at least one recess configured for disposal of the first spinal rod.

5. The kit recited in claim 1, wherein the one or more connectors each comprise spaced apart recesses each configured for disposal of the first spinal rod.

6. The kit recited in claim 1, wherein the cavity of the one or more connectors comprises a substantially rectangular cross-section.

7. The kit recited in claim 1, wherein the second spinal rod includes a first portion and a second portion, the second portion extending at an acute angle relative to the first portion.

8. The kit recited in claim 1, wherein the second spinal rod includes a first linear portion and a second linear portion, the second linear portion extending at an acute angle relative to the first linear portion.

9. The kit recited in claim 1, wherein the one or more connectors are each monolithic.

10. The kit recited in claim 1, wherein the bone fastener comprises the receiver; the receiver being configured for disposal of the first spinal rod.

11. The kit as recited in claim 1, wherein a position of the first spinal rod and a position of the second spinal rod do not overlap along the second axis.

12. A kit for spinal revision surgery, the kit comprising:

a first bone fastener;

one or more set screws each including a first thread and a second thread, the first thread being configured for engagement with a thread of a receiver of the first bone fastener, the first bone fastener having a first spinal rod at least partially disposed in the receiver;

one or more connectors each comprising a body, the body defining an aperture configured for disposal of one of the set screws, the body comprising opposite inner and outer surfaces, the inner surface defining a cavity configured for disposal of the receiver, the one or more connectors each including a second spinal rod extending from the outer surface;

one or more nuts each configured for engagement with the second thread of the one or more connectors; and a second bone fastener, the second bone fastener comprising a receiver configured for disposal of one of the second spinal rods of the one or more connectors, the one or more connectors each comprising spaced apart recesses configured for disposal of the first spinal rod below the second spinal rod extending from the outer surface of the one or more connectors; and wherein an anterior edge of the second spinal rod is substantially coplanar with an anterior end of the first thread along a first plane, and wherein a posterior edge of the second spinal rod is substantially coplanar with a second plane, wherein the first and second planes are normal to a first axis that is substantially transverse to a second axis defined along a length of the second spinal rod.

13. The kit recited in claim 12, wherein the body of each of the one or more connectors comprises a plurality of adjacently disposed walls that collectively define a sleeve with the aperture configured for disposal of one of the set screws; the plurality of adjacently disposed walls comprising two side walls, a proximal wall and an opposite distal wall adjacently disposed to the second spinal rod extending from the outer surface of the body.

14. The kit recited in claim 13, wherein the proximal wall and the opposite distal wall are perpendicularly disposed to the second spinal rod extending from the outer surface of the body; one of the spaced apart recesses disposed on a bottom portion of the proximal wall, and another of the spaced apart recesses disposed on a bottom portion of the distal wall.

15. The kit as recited in claim 12, wherein a peak of the recesses of the one or more connectors is below the anterior edge of the second spinal rod proximate to the body of the one or more connectors along the first axis.

16. The kit as recited in claim 15, wherein the anterior edge of the second spinal rod is above a posterior edge of the first spinal rod proximate to the body of the one or more connectors along the second axis.

17. A kit for spinal revision surgery, the kit comprising:

one or more first bone fasteners;

one or more first spinal rods;

one or more set screws each including a first thread and a second thread, the first thread being configured for engagement with a thread of a receiver of one of the first bone fasteners, the first bone fasteners each having one of the spinal rods at least partially disposed in the receiver;

one or more monolithic connectors each comprising a body, the body defining an aperture configured for disposal of one of the set screws, the body comprising opposite inner and outer surfaces, the inner surfaces each defining a cavity configured for disposal of a receiver of one of the one or more first bone fasteners, the cavity having a substantially rectangular cross-section, the one or more connectors each including a second spinal rod extending from the outer surface, one or more nuts each configured for engagement with the second thread of the one or more set screws;

and a second bone fastener, the second bone fastener comprising a receiver configured for disposal of one of the second spinal rods of the one or more connectors, the receiver of the first bone fasteners defining a groove, and the one or more first bone fasteners each comprising a head, a crown, and a band;

the crown being positioned in a cavity of the receiver of the first bone fasteners in confronting relation to the first spinal rod disposed in the receiver of the first bone fasteners;

the head of the one or more first bone fasteners being disposed in a spaced apart relation to the first spinal rod disposed in the receiver of the first bone fasteners;

the band being positioned in the groove such that the band directly engages the head of the bone fasteners;

the one or more connectors each comprising spaced apart recesses configured for disposal of one of the one or more first spinal rods below the second spinal rods extending from the outer surface of the one or more connectors;

wherein an anterior edge of the second spinal rod is substantially coplanar with an anterior end of the first thread along a first plane, and wherein a posterior edge of the second spinal rod is substantially coplanar with a posterior end of the first thread along a second plane, wherein the first and second planes are normal to a first axis that is substantially transverse to a second axis defined along a length of the second spinal rod;

and wherein a height of the first thread is substantially equivalent to a thickness of the second spinal rod.

* * * * *